United States Patent
Yadollahi et al.

(10) Patent No.: US 10,506,969 B2
(45) Date of Patent: Dec. 17, 2019

(54) ACOUSTIC UPPER AIRWAY ASSESSMENT SYSTEM AND METHOD, AND SLEEP APNEA ASSESSMENT SYSTEM AND METHOD RELYING THEREON

(71) Applicant: UNIVERSITY HEALTH NETWORK, Toronto (CA)

(72) Inventors: Azadeh Yadollahi, Toronto (CA); Frank Rudzicz, Toronto (CA); Shumit Saha, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 505 days.

(21) Appl. No.: 15/169,524

(22) Filed: May 31, 2016

(65) Prior Publication Data

US 2017/0119303 A1     May 4, 2017

Related U.S. Application Data

(60) Provisional application No. 62/250,040, filed on Nov. 3, 2015.

(51) Int. Cl.
*A61B 5/00* (2006.01)
*A61B 5/08* (2006.01)
(Continued)

(52) U.S. Cl.
CPC .............. *A61B 5/4818* (2013.01); *A61B 5/08* (2013.01); *A61B 5/11* (2013.01); *A61B 5/6822* (2013.01);
(Continued)

(58) Field of Classification Search
CPC ....... A61B 5/4818; A61B 5/4806; A61B 5/08; A61B 5/0826; A61B 5/113; A61B 5/6822
See application file for complete search history.

(56) References Cited

U.S. PATENT DOCUMENTS

| | | |
|---|---|---|
| 4,648,407 A | 3/1987 | Sackner |
| 5,671,733 A | 9/1997 | Raviv et al. |

(Continued)

FOREIGN PATENT DOCUMENTS

| | | |
|---|---|---|
| CA | 2585824 A1 | 9/2008 |
| EP | 2653108 A1 | 10/2013 |

(Continued)

OTHER PUBLICATIONS

Nakano, Hiroshi, et al. "Validation of a new system of tracheal sound analysis for the diagnosis of sleep apnea-hypopnea syndrome." Sleep-New York Then Westchester-27.5 (2004): 951-958.

(Continued)

*Primary Examiner* — Max F Hindenburg
(74) *Attorney, Agent, or Firm* — SoCal IP Law Group LLP; Mark Andrew Goldstein

(57) ABSTRACT

Described are various embodiments of an acoustic upper airway assessment system and method, and sleep apnea assessment system and method relying thereon. In one embodiment, a non-invasive method is described for assessing upper airway anatomy in a subject while breathing. This method comprises receiving as input at a hardware processor a digital signal representative of respiratory sounds generated by the subject while breathing; isolating digital respiratory sound segments from said digital signal; computationally extracting a designated spectral feature from each of said segments to characterize said respiratory sounds within each of said segments; automatically evaluating each said extracted spectral feature against a preset upper airway anatomy metric associated with said designated spectral feature to characterize a given upper airway anatomy measure in the subject while breathing; and outputting a sleep apnea severity indication based on said characterized upper airway anatomy measure.

23 Claims, 14 Drawing Sheets

(51) Int. Cl.
*A61B 5/11* (2006.01)
*A61B 7/00* (2006.01)
(52) U.S. Cl.
CPC ............ *A61B 5/7246* (2013.01); *A61B 5/742* (2013.01); *A61B 5/7475* (2013.01); *A61B 7/003* (2013.01); *A61B 5/7257* (2013.01); *A61B 2562/0204* (2013.01); *A61B 2562/0219* (2013.01)

(56) References Cited

U.S. PATENT DOCUMENTS

| | | | |
|---|---|---|---|
| 5,782,240 | A | 7/1998 | Raviv et al. |
| 5,797,852 | A | 8/1998 | Karakasoglu et al. |
| 5,845,636 | A | 12/1998 | Gruenke et al. |
| 5,961,447 | A | 10/1999 | Raviv et al. |
| 6,045,514 | A | 4/2000 | Raviv et al. |
| 6,142,950 | A | 11/2000 | Allen et al. |
| 6,171,258 | B1 | 1/2001 | Karakasoglu et al. |
| 6,213,955 | B1 | 4/2001 | Karakasoglu et al. |
| 6,290,654 | B1 | 9/2001 | Karakasoglu |
| 6,368,287 | B1 | 4/2002 | Hadas |
| 6,375,623 | B1 | 4/2002 | Gavriely |
| 7,118,536 | B2 | 10/2006 | Haberland et al. |
| 7,225,021 | B1 | 5/2007 | Park et al. |
| 7,387,124 | B2 | 6/2008 | Noda et al. |
| 7,785,265 | B2 | 8/2010 | Schätzl |
| 7,850,619 | B2 | 12/2010 | Gavish et al. |
| 9,844,336 | B2 * | 12/2017 | Zigel .................... A61B 5/4818 |
| 10,194,834 | B2 * | 2/2019 | Selvaraj ............... A61B 5/0806 |
| 2002/0123699 | A1 | 9/2002 | Lambert et al. |
| 2005/0222502 | A1 | 10/2005 | Cooper |
| 2006/0008745 | A1 | 1/2006 | Sasaki et al. |
| 2006/0196510 | A1 | 9/2006 | McDonald et al. |
| 2006/0266356 | A1 | 11/2006 | Solos et al. |
| 2008/0001735 | A1 | 1/2008 | Tran |
| 2008/0030105 | A1 | 2/2008 | Florian et al. |
| 2008/0243017 | A1 | 10/2008 | Moussavi et al. |
| 2008/0319333 | A1 | 12/2008 | Gavish et al. |
| 2009/0118631 | A1 | 5/2009 | Gavish et al. |
| 2009/0293880 | A1 | 12/2009 | Rutan |
| 2010/0240982 | A1 | 9/2010 | Westbrook et al. |
| 2011/0105915 | A1 | 5/2011 | Bauer et al. |
| 2012/0058727 | A1 | 3/2012 | Cook et al. |
| 2014/0188006 | A1 | 7/2014 | Alshaer et al. |

FOREIGN PATENT DOCUMENTS

| | | |
|---|---|---|
| GB | 2214302 A | 8/1989 |
| WO | 2000019895 A1 | 4/2000 |
| WO | 2001015602 A1 | 3/2001 |
| WO | 2001093743 A2 | 12/2001 |
| WO | 2010054481 A1 | 5/2010 |
| WO | 2011010384 A1 | 1/2011 |
| WO | 2012155257 A1 | 11/2012 |
| WO | 2016000061 A1 | 1/2016 |

OTHER PUBLICATIONS

Varady, Peter, et al. "A Novel Method for the Detection of Apnea and Hypopnea Events in Respiration Signals", IEEE Transactions on Biomedical Engineering, IEEE Service Center, Piscataway, NJ, USA, vol. 49, No. 9, Sep. 1, 2002, p. 936-942.

Yadollahi, A. et al., "Relationship of Respiratory Sounds to Alternation in the Upper Airway Resistance", Engineering in Medicine and Biology Science (EMBC), Conference Proceedings: 34th Annual International Conferene of the IEEE, Sep. 1, 2012, pp. 3648-3651.

Yadollahi, A. et al., Variations in Respiratory Sounds in Relation to Fluid Accumulation in the Upper Airways:, Engineering in Medicine and Biology Science (EMBC), Conference Proceedings: 35th Annual International Conferene of the IEEE, Jul. 7, 2013, pp. 2924-2927.

* cited by examiner

ACOUSTIC UPPER AIRWAY ASSESSMENT SYSTEM AND METHOD, AND SLEEP APNEA ASSESSMENT SYSTEM AND METHOD RELYING THEREON

RELATED APPLICATION

This patent claims benefit of Provisional Patent Application No. 62/250,040 filed Nov. 3, 2015, entitled Acoustic Upper Airway Assessment System, Method and Model, and Sleep Apnea Assessment System and Method Relying Thereon.

FIELD OF THE DISCLOSURE

The present disclosure relates to upper airway assessment techniques, and, in particular, to an acoustic upper airway assessment system and method, and sleep apnea assessment system and method relying thereon.

BACKGROUND

Snoring, common in 20 to 40% of adult population, is one of the main symptoms of obstructive sleep apnea (OSA). Sleep apnea occurs due to the repetitive partial or complete collapse of the upper airway during sleep. Upper airway narrowing can increase the speed of airflow and pressure drop along the upper airway, which will consequently increase turbulence of airflow within the upper airways. This sequence of events will cause vibration of pharyngeal tissue that can induce snoring. Snoring sound varies not only from person to person but also varies for the same person during sleep depending on the level of upper airway narrowing.

As previously reported, for example in Applicant's co-pending International Application No. PCT/CA2014/050627, the entire contents of which are incorporated herein by reference, gravity and a sedentary lifestyle can cause fluid accumulation in the legs during the day. When lying down to sleep, part of this fluid moves out of the legs and accumulates in the neck. Fluid accumulation in the neck can increase neck circumference (NC), narrow the upper airway, and increase upper airway resistance and collapsibility. As such, it is believed that fluid accumulation in the neck can worsen OSA.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

A need exists for an acoustic upper airway assessment system and method that overcome some of the drawbacks of known techniques, or at least, provides a useful alternative thereto. A further need exists for a sleep apnea assessment system and method, for example, that rely on such upper airway assessments. Some aspects of this disclosure provide examples of such acoustic upper airway assessment systems and methods, and sleep apnea assessment systems and methods relying thereon.

In accordance with one aspect, there is provided a non-invasive method for assessing upper airway anatomy in a subject while breathing, the method comprising: receiving as input at a hardware processor a digital signal representative of respiratory sounds generated by the subject while breathing; isolating digital respiratory sound segments from said digital signal; computationally extracting a designated spectral feature from each of said segments to characterize said respiratory sounds within each of said segments; automatically evaluating each said extracted spectral feature against a preset upper airway anatomy metric associated with said designated spectral feature to characterize a given upper airway anatomy measure in the subject while breathing; and outputting a sleep apnea severity indication based on said characterized upper airway anatomy measure.

In one embodiment, the designated spectral feature is an average snoring sound power within a given frequency range, and wherein said upper airway anatomy metric is a neck circumference variation metric defined by a pre-established snoring power scale automatically correlating a relatively higher snoring power with a correspondingly larger neck circumference increase.

In one embodiment the designated spectral feature is a predominant snoring frequency, such as one of a pitch frequency, a first formant frequency and a second formant frequency of said snoring sound segments, and wherein said upper airway anatomy metric is an effective pharyngeal length metric defined by a pre-established frequency scale automatically correlating a relatively lower predominant frequency with a correspondingly greater effective pharyngeal length.

In one embodiment, the designated spectral feature is a predominant frequency, such as a pitch frequency, and wherein said upper airway anatomy metric is a neck fluid volume NFV variation defined by a pre-established NFV scale automatically correlating a relatively lower predominant frequency with a correspondingly greater NFV increase.

In accordance with another aspect, there is provided a non-invasive method for evaluating sleep apnea severity, the method comprising: receiving as input at a hardware processor a digital signal representative of respiratory sounds generated by the subject while breathing; isolating digital snoring sound segments from said digital; computationally extracting a designated spectral feature from each of said segments to characterize said snoring sounds within each of said segments; automatically evaluating each said extracted designated spectral feature against a preset sleep apnea severity metric associated with said designated spectral feature; and outputting a sleep apnea severity indication based on said metric; wherein said designated spectral feature comprises at least one of an average snoring sound power and a predominant snoring frequency, and wherein said metric comprises correlating a relatively higher snoring power and a relatively lower predominant frequency, respectively, with a correspondingly higher sleep apnea severity.

In accordance with another aspect, there is provided a non-invasive upper airway anatomy assessment device comprising: an acoustic signal input interface; a digital storage device having stored thereon an upper airway assessment engine operable to access an upper airway anatomy metric associated with a designated respiratory sound spectral feature; and a hardware processor operable to execute said engine to: receive as input a digital signal representative of respiratory sounds generated by a given subject while breathing; isolate digital respiratory sound segments from said respiratory sounds; extract said designated spectral feature from each of said segments to characterize said respiratory sounds within each of said segments; evaluate each said extracted spectral feature against said metric to characterize a given upper airway anatomy of the given subject while breathing; and output a sleep apnea severity indication based on said given upper airway anatomy so characterized.

In one embodiment, the device further comprises a microphone operatively coupled to said acoustic signal input interface and to be located in an area of the given subject while breathing to capture said respiratory sounds and generate said digital signal representative thereof.

In accordance with another aspect, there is provided a non-transitory computer-readable medium having statements and instructions stored therein for execution by a processor to execute an upper airway assessment engine to: receive as input a digital signal representative of respiratory sounds generated by a given subject while breathing; isolate digital respiratory sound segments from said digital signal; extract a designated spectral feature from each of said segments to characterize said respiratory sounds within each of said segments; access an upper airway anatomy metric corresponding to said designated spectral feature; evaluate each said extracted spectral feature against said upper airway anatomy metric to characterize a given upper airway anatomy of the given subject while breathing; and output a sleep apnea severity indication based on said given upper airway anatomy so characterized.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 7A is an acoustic signal plot identifying extracted snoring segments from a 10 second breathing sound recording, whereas

FIGS. 8A to 8D schematically illustrate a model for snore sound generation and propagation, as considered within various embodiments of the present disclosure, in which FIG. 8A is a snore PSD plot identifying exemplary formant frequencies; FIG. 8B is a block diagram of the snore generation and propagation model considered herein, alongside an electrical equivalent circuit of a pharyngeal tube with non-rigid wall with a transfer function of the circuit ($R_a$, resistance; $L_a$, inertance; $C_a$, compliance; $G_a$, conductance; $L_w$, wall inertance; $R_w$, wall resistance; $C_w$, wall compliance); FIG. 8C is a flow diagram of snore generation and propagation; FIG. 8D is a diagram of an upper airway anatomy showing a measured upper airway area, neck diameter, and wall thickness used in the model, along with an illustrative placement of a microphone used in acquiring acoustic signals for implementation of the systems and methods considered herein;

FIG. 9A is a plot of an average and standard deviation of snoring power in various frequency ranges for different sleep stages, whereas

FIG. 10A is a scatterplot of a first formant (F1) identified for recorded snores against corresponding simulated formants from the pharyngeal tube model; whereas

DETAILED DESCRIPTION

The systems and methods described herein provide, in accordance with different embodiments, different examples in which breathing sounds, such as snoring, can be automatically assessed against a pre-established upper airway sound generation and propagation model to characterize upper airway anatomy variations and/or features that may be associated with, or responsible for, a particular breathing disorder, such as sleep apnea. In some embodiments, these acoustic upper airway assessments can lead or contribute to an accurate screening for, diagnosis or characterization of such a disorder.

In accordance with some aspects of the herein-described embodiments, an acoustic upper airway assessment system and method will now be described. In particular, the systems and methods considered herein rely on acoustic variations observed in relation to variations in the upper airway anatomy, such as in the pharynx, for example. For example, the methods and systems described herein can be used to non-invasively assess various parameters associated with upper airway narrowing, and OSA in some instances, by identifying acoustic changes in respiratory sounds resulting therefrom.

For instance, tracheal sound analysis, in the context of the below-described embodiments, can provide an effective and non-invasive way to investigate variations in the physiology of the airways and monitor upper airway obstruction during both wakefulness and sleep. Different mechanisms including turbulence of respiratory airflow and pressure fluctuations in the pharynx can contribute to the generation of tracheal sounds. In some embodiments, the vibrations so generated are transmitted to the skin through the tracheal wall and tissue beneath the skin, and can be picked up by a microphone placed over the trachea, for example, but also for example via a microphone mounted to or in the ear, the cheek, a face mask disposed above a nose and mouth area of the subject's face, or again, but subject to greater ambient noise, freestanding, mounted or positioned in a room near the subject. For example, ambient and other noise may be reduced upon positioning the microphone in skin-contact with the subject, for example in a throat, cheek or ear area.

Figure 1:
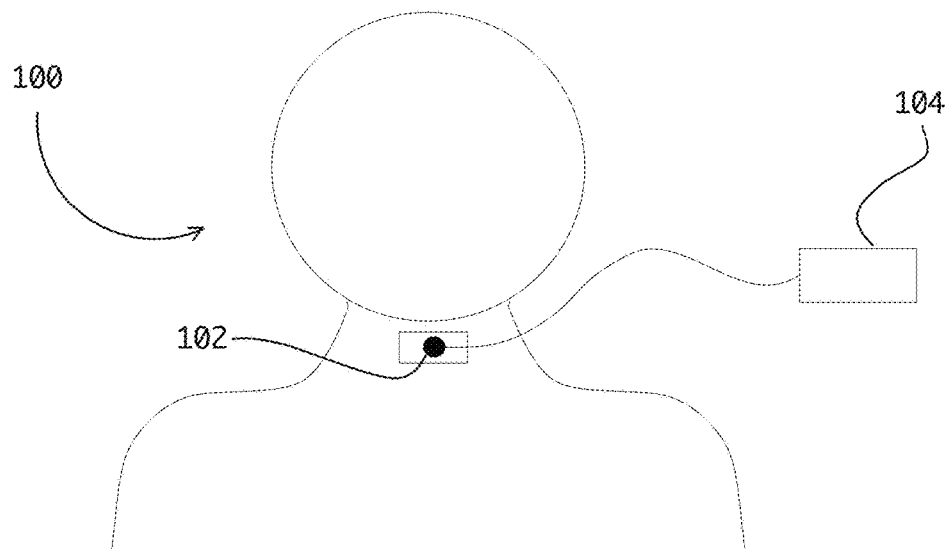
FIG. 1 is a schematic diagram of a breathing sound assessment system, in accordance with one embodiment.

With reference now to FIG. 1, and in accordance with one embodiment, a system for assessing respiratory sounds, generally referred to using the numeral 100, will now be described. In this example, the system 100 generally comprises a microphone 102 or the like to be attached on the surface of a throat area of a candidate for acquiring acoustic sounds and/or signals over time. The microphone 102 is operatively coupled to a data processing device 104 having stored and implemented thereon one or more upper airway assessment tools/engines to automatically process the acquired data according to one or more designated assessment protocols for output. While the data processing device 104 is illustrated in FIG. 1 as distinct from the microphone/recording device 102, in some embodiments, the microphone 102 and data processing device 104 may be integral to or combined in a common data recording device to be worn on the subject's neck area, for example. While the term "data processing device" is used generically herein to refer not only to a device for performing automated or semi-automated acoustic upper airway assessments, it may also refer to similar devices also configured for the detection or assessment of other more or less related conditions, symptoms, and/or biological processes.

The processing device 104 is depicted herein as a distinctly implemented device operatively coupled to microphone 102 for communication of data thereto, for example, via one or more data communication media such as wires, cables, optical fibres, and the like, and/or one or more wireless data transfer protocols, as would be readily appreciated by one of ordinary skill in the art. The processing device may, however, in accordance with other embodiments, be implemented integrally with a recording device embodying the microphone (e.g. within the context of a self-contained assessment tool or device that can be secured to or on the subject's body during data acquisition and processing), for example, depending on the intended practicality of the system 100, and/or context within which it is to be implemented. As will be appreciated by the skilled artisan, the processing device 104 may further or alternatively be coupled to, or operated in conjunction with, an external processing and/or interfacing device, such as a local or remote computing device or platform provided for the further processing and/or display of raw and/or processed data, or again for the interactive display of system implementation data, protocols and/or screening/assessment tools.

In one embodiment, the system may further comprise an accelerometer (not shown) or the like, to track a position and/or movement of the subject's head, neck and/or pharynx, for example relative to the trunk, in correlating such position and/or movement with output assessments. Such correlations may then be used to better evaluate a legitimacy, accuracy and/or relevance of the output assessment(s), and/or provide guidance in establishing treatment protocols and/or guidelines to address certain conditions, symptoms and/or disorders experienced by the subject and characterized, highlighted and/or identified by the assessments generated by the methods and systems described herein.

Figure 2:
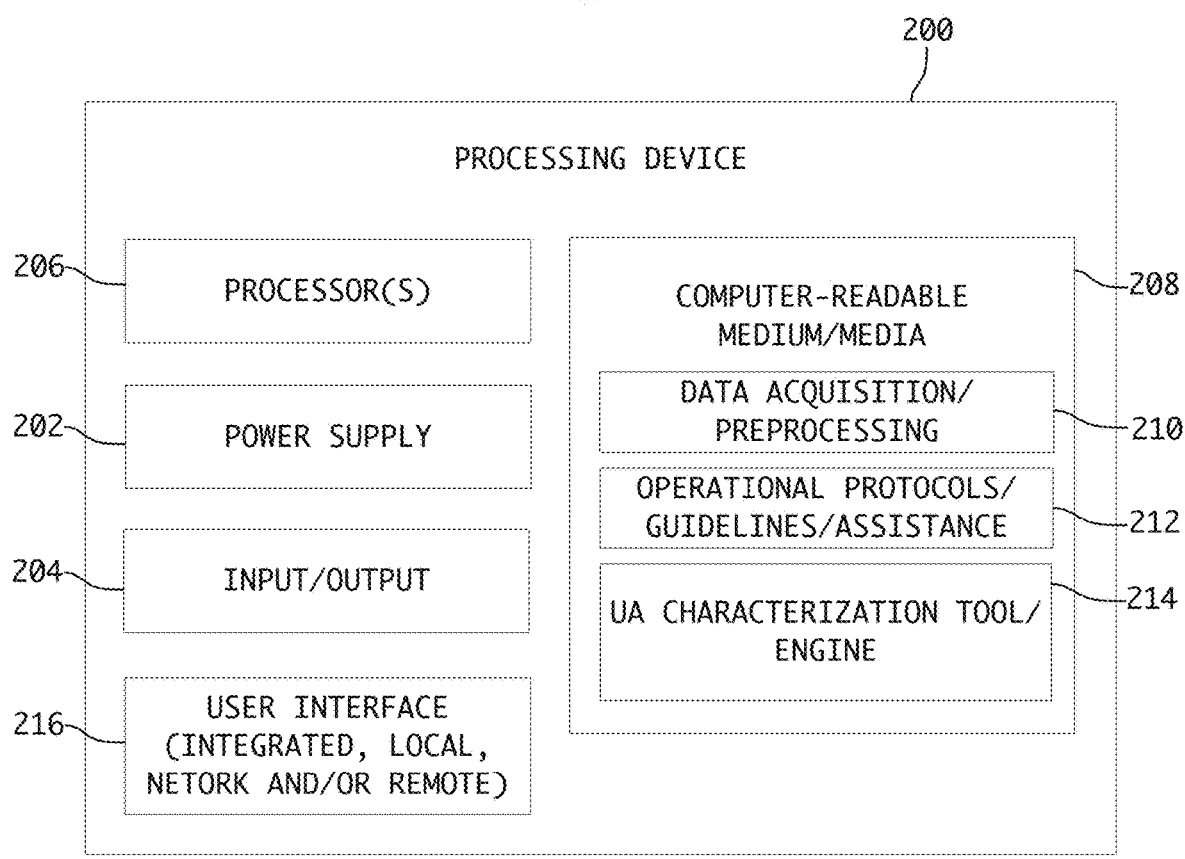
FIG. 2 is a schematic diagram of a breathing sound assessment device, and components thereof, in accordance with one embodiment.

With reference to FIG. 2, the processing device, depicted herein generically as a self-contained device 200, generally comprises a power supply 202, such as a battery or other known power source, and various input/output port(s) 204 for the transfer of data, commands, instructions and the like with interactive and/or peripheral devices and/or components (not shown), such as for example, a distinctly operated microphone and/or acoustic data recorder, external data processing device, display or the like. The device 200 further comprises one or more computer-readable media 208 having stored thereon statements and instructions for implementation by one or more processors 206 in automatically implementing various computational tasks with respect to, for example, acoustic data acquisition and processing 210, operation of the device 212 (e.g. one or more clinically accepted operating protocols, testing and/or validation sequences, etc.), or again in the implementation of one or more acoustic assessment tools/engines (e.g. upper airway (UA) characterization tool/engine 214) implemented on or in conjunction with the device 200. The device 200 may further comprise a user interface 216, either integral thereto, or distinctly and/or remotely operated therefrom for the input of data and/or commands (e.g. keyboard, mouse, scroll pad, touch screen, push-buttons, switches, etc.) by an operator thereof, and/or for the presentation of raw, processed and/or assessment data outputs (e.g. graphical user interface such as CRT, LCD, LED screen, touchscreen, or the like, visual and/or audible signals/alerts/warnings/cues, numerical displays, etc.)

As will be appreciated by those of ordinary skill in the art, additional and/or alternative components operable in conjunction and/or in parallel with the above-described illustrative embodiment of device 200 may be considered herein without departing from the general scope and nature of the present disclosure. It will further be appreciated that device 200 may equally be implemented as a distinct and dedicated device, such as a dedicated home, clinical or bedside assessment device, or again implemented by a multi-purpose device, such as a multi-purpose clinical or bedside device, or again as an application operating on a conventional computing device, such as a laptop or PC, or other personal computing devices such as a PDA, smartphone, tablet or the like.

In the illustrative example of FIG. 2, the stored statements and instructions of computer-readable medium 208 encompass one or more acoustic assessment tools/engines 214 that, when launched via processor 206, act on acquired acoustic data to output one or more assessments useful in characterizing an upper airway of the subject's neck, for example.

In accordance with some embodiments, the assessment tool/engine 214 may be configured to receive as input (e.g. via input port 204) acoustic data of interest acquired, for example, via a recording device and/or microphone, such as microphone 102 of FIG. 1. In some embodiments, the engine will include one or more preprocessing utilities (e.g. to pre-process, filter and/or segment the raw data according to designated pre-processing routines), a feature extraction utility (e.g. to automatically compute, extract and process one or more designated acoustic features of the recorded and optionally preprocessed respiratory sounds), a feature characterization utility (e.g. to automatically characterize extracted features as corresponding to one or more designated acoustic respiratory sound classes and/or categories associated with a particular upper airway characterization and/or breathing condition), and one or more optional post-processing utilities, the latter generating a global or respective outputs to be rendered or otherwise provided via the system's input/output port 204 and/or user interface 216.

As will be exemplified in the below-detailed studies, various respiratory sound characterizations can be automatically obtained via the development and validation of a subject-specific upper airway sound generation and propagation model, which model can then be used to accurately predict upper airway anatomy variations and perturbations resulting in, or contributing to, quantifiable breathing disorder characterizations, such as provided by a sleep apnea severity or apnea-hypopnea index (AHI).

The objective of the below-reported studies was to investigate whether fluid accumulation in the neck during sleep and the consequent narrowing in the upper airway would impact various time and frequency domain snoring characteristics in patients with sleep apnea. The effects of changes in neck circumference (NC), neck length, neck-fluid volume (NFV) and upper airway cross-sectional area (UA-XSA) were thus observed during sleep on snoring sound characteristics, resulting in the identification of reliable features for the automated characterization of respiratory sounds for the purposes of upper airway anatomy and related sleep disorder assessments.

The following provides different examples, in accordance with some aspects of the above-described embodiments, of upper airway assessment methods, systems and models, and their related utility in contributing to accurate assessments of related breathing disorders such as OSA. It will be appreciated by the skilled artisan that these examples are not intended to limit the general scope and nature of the present disclosure, but rather provide evidence as to the utility, applicability and/or accuracy of the methods and systems described herein in accordance with different embodiments of the invention.

EXAMPLE 1

In this example, men in the age range of 20-70 years old and of body mass index (BMI)<30 kg/m$^2$ were included. Exclusion criteria were a history of cardiovascular, renal, neurological or respiratory diseases, or taking any medication that might influence fluid retention.

Participants underwent a daytime sleep study, and slept in supine position only. Their sleep was assessed by regular polysomnography to score sleep stages, arousals, and sleep apnea severity as detected by the apnea/hypopnea index (AHI), which indicates the number of apneas and hypopneas per hour of sleep. In all participants, neck circumference (NC) was measured before and immediately after sleep while supine, and was measured using a measuring tape above the cricothyroid cartilage.

Tracheal sounds were recorded by a Sony EMC-44B omni-directional microphone placed over the suprasternal notch of the neck. Snore sounds were amplified and filtered by a low-pass filter (cut off frequency: 5 kHz) using Biopac DA100C, and digitized at a sampling rate of 12.5 kHz using a MP150 Biopac System.

In this example, tracheal sound recordings included snore, breathing, and heart sounds. An expert manually extracted snoring sound segments from tracheal sound recordings by listening to the sounds and investigating them in the time-frequency domain. A computerized program (e.g. PRAAT) for labeling audio data was used to label and export the identified snoring sound segments.

After segmentation, different snoring sound features in both time and frequency domains were extracted for the entire sleep time as well as for the rapid eye movement (REM) sleep stage and stages N1, N2 and N3 of non-REM sleep. The calculated features in the time domain were:
Snoring Percentage (SP), which represents the number of snores in each sleep stage divided by the total number of snores in the entire sleep;
Snoring Index (SI), which represents the number of snores in each sleep stage divided by the total sleeping time (in hours).
Snoring Time Index (STI), which represents the total snoring time divided by the time spent in each sleep stage.

In this example, all the snoring segments were filtered in the frequency range of 100 to 4000 Hz to remove the effects of heart sounds in the low frequency components as well as high frequency noises. The power spectral density (PSD) of snoring segments was estimated using a Hamming window of 100 ms duration and 50% overlap between adjacent windows. From the PSD, the frequency domain features were calculated as the average power (in dB) of each snoring segment in different frequency ranges: 100-4000 Hz, 100-150 Hz, 150-450 Hz, 450-600 Hz, 600-1200 Hz, 1200-1800 Hz, 1800-2500 Hz and 2500-4000 Hz.

The change in NC before and after sleep was assessed by paired t-test with a significance level of P<0.05. Correlations between the snoring sound characteristics and changes in NC were investigated by Pearson or Spearman's rank coefficient with the significance level set at P<0.05.

Results

Among the 15 men participated in the study, two did not snore at all. They were included in the time domain analysis but excluded from the frequency domain analysis. Table 1 shows the baseline characteristics and sleep parameters of the participants. From before and after sleep, there were significant increases in NC (ΔNC: 0.51±0.4 cm, P<0.01).

TABLE 1

Characteristics of the Participants (n = 15)

| Baseline Characteristics | | Sleep Structure | |
|---|---|---|---|
| Variable | Mean ± STD | Variable | Mean ± STD |
| Age, years | 43.5 ± 13.5 | Total Sleep Time, min | 136.2 ± 46.0 |
| Height, cm | 178.2 ± 5.5 | Stage N1 sleep, % | 21.8 ± 8.5 |
| Weight, kg | 80.3 ± 9.7 | Stage N2 sleep, % | 52.4 ± 15.4 |
| BMI, kg/m2 | 25.4 ± 3.2 | Stage N3 sleep, % | 16.0 ± 16.5 |
| NC, cm | 42.2 ± 3.0 | REM sleep, % | 7.5 ± 6.4 |
| | | Sleep efficiency, % | 65.5 ± 17.1 |
| | | Total AHI, /h | 33.6 ± 24.8 |

Table 2 depicts the average and standard deviation of time domain features of snore sounds in every sleep stage and over total sleep time. Participants had an average of 175 snoring events per hour of sleep. The percentage of snoring sounds in Stage 2 of sleep was significantly higher than other sleep stages (P<0.01).

TABLE 2

Average and Standard Deviation of Time Domain features of Snoring Sounds

|  | Stage N1 | Stage N2 | Stage N3 | REM | Total Sleep |
|---|---|---|---|---|---|
| Snoring Percentage, % | 11.2 ± 9.4 | 44.7 ± 29.6 | 27.3 ± 32.4 | 3.4 ± 5.2 |  |
| Snoring Index, /h | 106.8 ± 133.5 | 138.1 ± 112.1 | 257.2 ± 303.0 | 74.2 ± 5.7 | 174.7 ± 124.1 |
| Snoring Time Index, % | 3.2 ± 4.4 | 4.4 ± 4.1 | 6.2 ± 7.3 | 2.7 ± 3.6 | 4.9 ± 3.8 |

Figure 3:
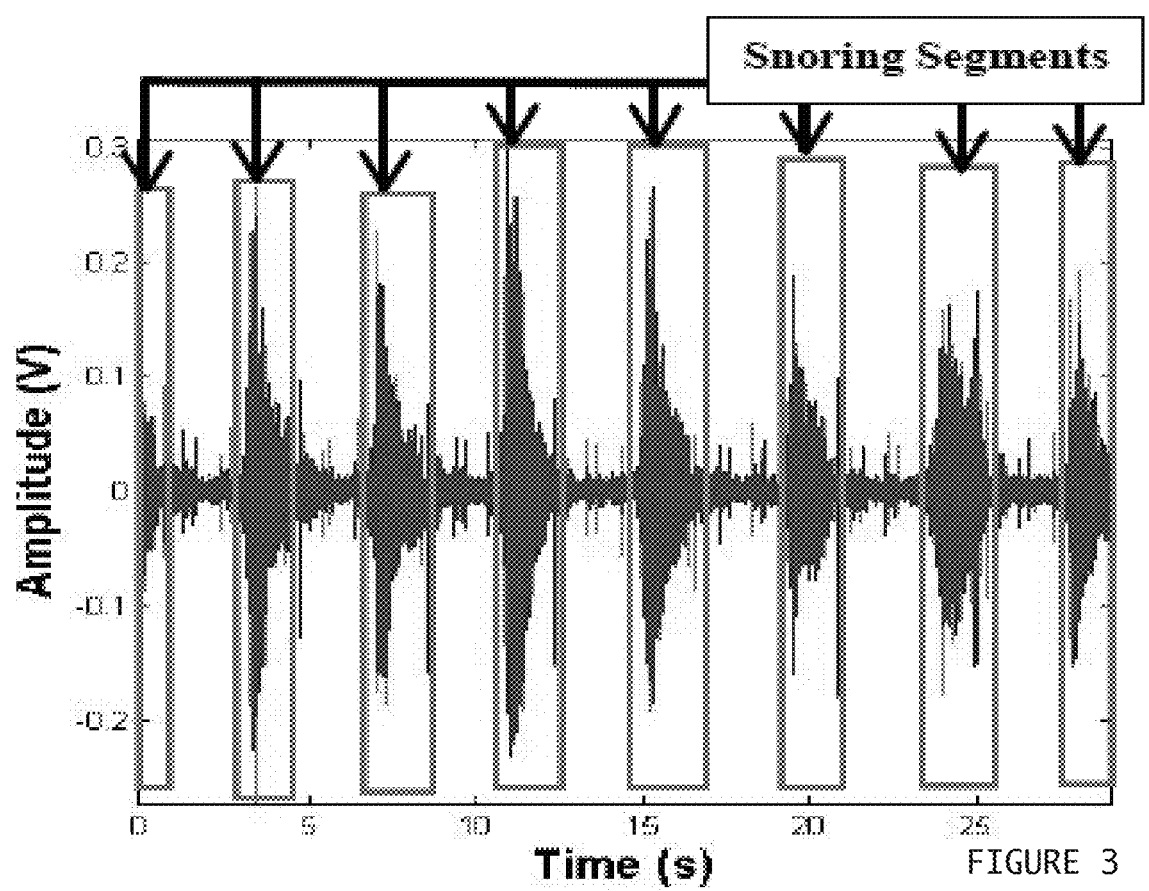
FIG. 3 is an illustrative acoustic signal plot identifying extracted snoring segments from a 30 second breathing sound recording, in accordance with a first example.
Figure 4:
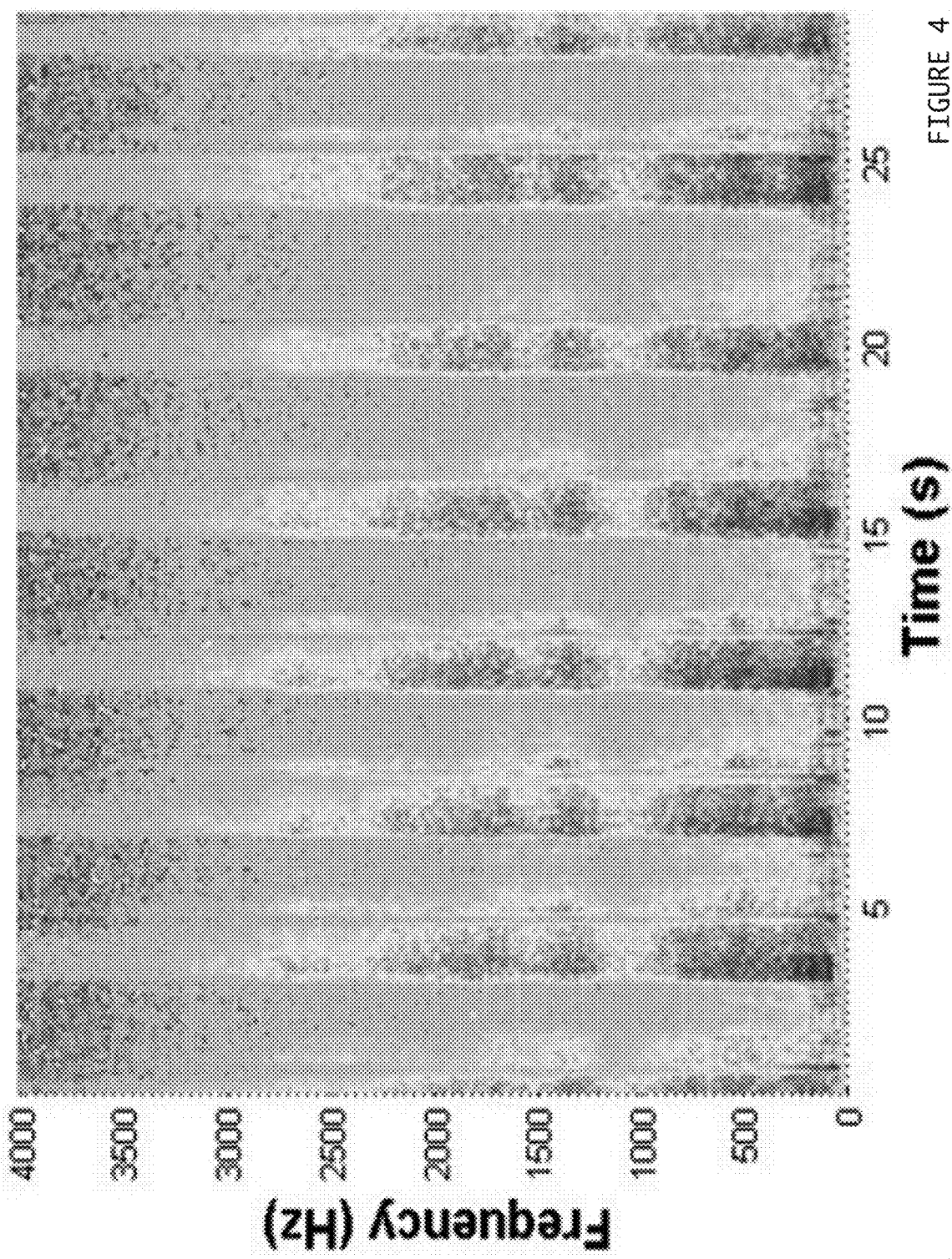
FIG. 4 is a spectrogram of the extracted snoring segments identified in FIG. 3.
Figure 5:
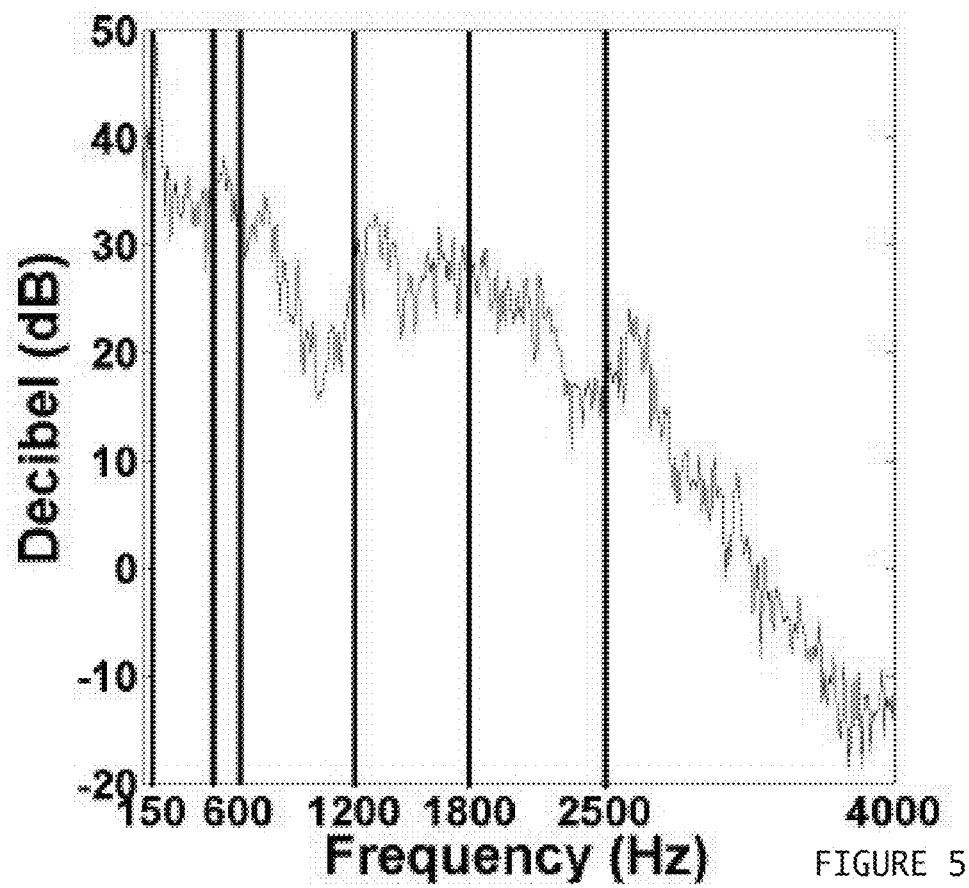
FIG. 5 is a plot of an estimated power spectral density (PSD) of the snoring segments identified in FIG. 1.

FIG. 3 shows an example of extracted snoring segments from a 30 second breathing segment; whereas FIG. 4 displays the spectrogram of these extracted snoring segments. It can be seen that compared to normal breathing, snoring segments have a higher intensity in all frequency components. FIG. 5 shows the estimated PSD of the snoring segments identified in FIG. 3. The marking in the PSD showed different frequency ranges as mentioned earlier. From FIG. 5, it is seen that the estimated PSD has a highest peak below 600 Hz. The average and standard deviation of snore sound average power in different frequency ranges and different sleep stages are shown in Table 3, below. In all sleep stages, snoring power was higher below the frequency of 600 Hz, and reduced above 600 Hz (P<0.01).

TABLE 3

Average and Standard Deviation of Snoring Power in Several Frequency Bands (dB)

| | Freq. (Hz) | | | | | | | |
|---|---|---|---|---|---|---|---|---|
|  | 100-4000 | 100-150 | 150-450 | 450-600 | 600-1200 | 1200-1800 | 1800-2500 | 2500-4000 |
| Stage N1 | 38.1 ± 3.8 | 50.8 ± 4.1 | 45.5 ± 4.1 | 40.1 ± 4.8 | 29.1 ± 5.4 | 24.4 ± 5.5 | 18.3 ± 6.1 | 6.2 ± 6.0 |
| Stage N2 | 38.3 ± 4.4 | 50.3 ± 4.7 | 46.1 ± 4.6 | 40.3 ± 3.9 | 30.1 ± 3.9 | 25.1 ± 4.4 | 18.8 ± 5.3 | 6.4 ± 6.1 |
| Stage N3 | 37.7 ± 5.3 | 49.2 ± 4.3 | 45.7 ± 5.9 | 39.7 ± 4.6 | 28.9 ± 4.7 | 25.3 ± 5.0 | 19.1 ± 6.9 | 8.1 ± 6.6 |
| REM | 36.5 ± 3.8 | 49.7 ± 3.6 | 43.6 ± 3.7 | 37.3 ± 4.8 | 28.1 ± 5.8 | 23.4 ± 6.7 | 18.4 ± 7.4 | 6.8 ± 7.2 |
| Total Sleep | 38.2 ± 4.1 | 50.6 ± 4.6 | 46.0 ± 4.3 | 40.5 ± 4.2 | 30.2 ± 4.3 | 25.5 ± 4.7 | 19.5 5.5 | 7.3 ± 6.0 |

The statistical analysis was performed to see the association between the snoring sound features and the change in NC. No strong correlation was found between the changes in NC, and the snoring index or the snoring time index. There were, however, significant and negative correlations between the percentage of snores in sleep Stage 3 and both the pre-sleep (r=−0.65, P=0.008) and post-sleep NC (r=−0.75, P=0.001). Similar correlations were found between the percentage of REM sleep snores and pre-sleep (r=−0.56, P=0.029) and post sleep NC (r=−0.55, P=0.032). These results suggest that participants with more snoring events spent less time in deep sleep stages.

Figure 6:
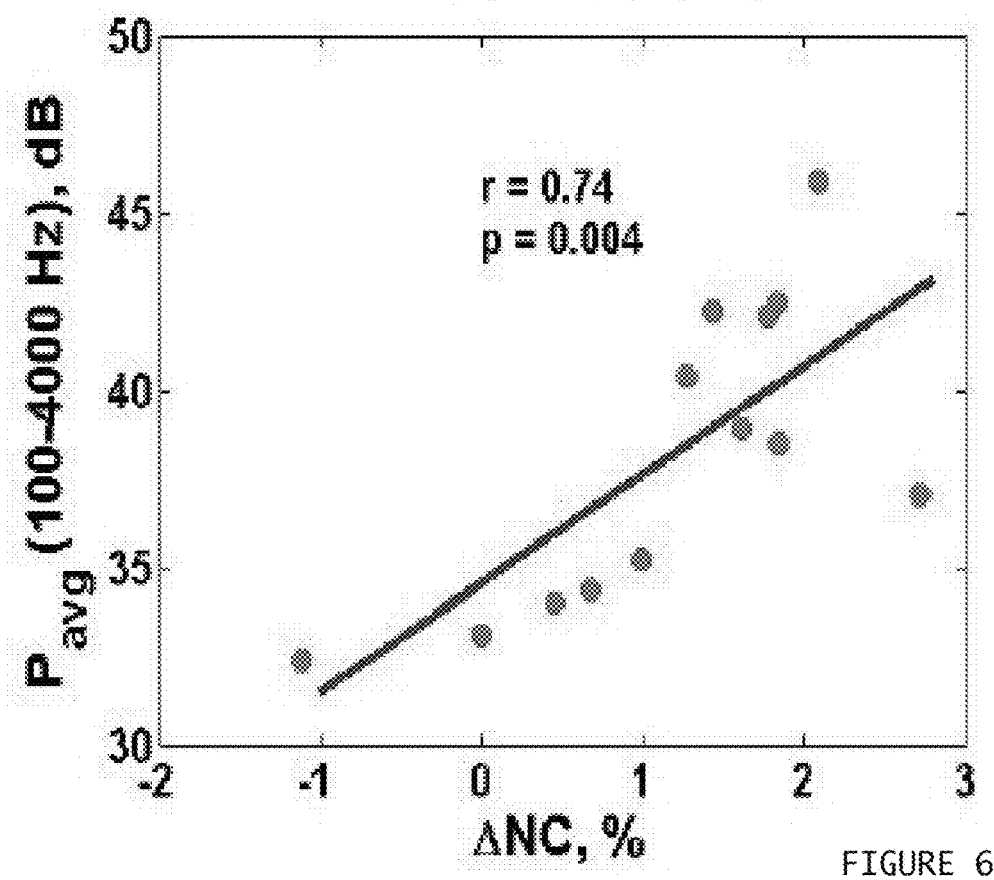
FIG. 6 is a plot identifying a relationship between a percentage change in neck circumference (NC) and average power of snoring sounds, as calculated over an entire sleep duration within a 100-4000 Hz frequency range, in accordance with the first example.

For total sleep, changes in NC were strongly correlated with the average power of the snoring sounds in the frequency range of 100-4000 Hz (i.e. see FIG. 6, r=0.74, P=0.004). Also, significant correlations were observed between the changes in NC and snoring sound power for frequency ranges 100-150 Hz (r=0.70, P=0.008), 150-450 Hz (r=0.73, P=0.005), and 450-600 Hz (r=0.65, P=0.025).

For sleep Stage 2, a similar correlation between NC and snoring power was found. For instance, the changes in NC were positively correlated with the average power of snoring sounds in the total frequency range of 100-4000 Hz (r=0.70, P=0.007, 100-150 Hz (r=0.68, P=0.011), 150-450 Hz (r=0.71, P=0.007), and 450-600 Hz (r=0.71, P=0.007).

In this illustrative study, the effects of change in NC during sleep on snoring sound characteristics were investigated. As noted above, it was observed that that an increase in NC increased a snoring sound average power in different frequency ranges. This could be due to the fact that fluid accumulation in the neck and the consequent increases in the NC could increase pharyngeal tissue pressure around the neck, narrow the upper airway, and consequently increase air turbulence in the upper airway and the snoring sound average power, consistent with the observation that increases in NC narrows the upper airway and increases sleep apnea severity. These results thus support the use of snoring sound analysis for monitoring the effects of fluid accumulation in the neck on the upper airway physiology and sleep apnea severity.

EXAMPLE 2

In this example, participants were recruited by advertisement. The inclusion criteria were non-obese men (body mass index of <30 kg/m$^2$) of 20-70 years of age and a blood pressure of ≤140/90 mmHg. Individuals with a history of cardiovascular, renal, neurological or respiratory diseases, taking any medication that might influence fluid retention, a previous diagnosis of OSA, or having less than one hour of sleep during the protocol were excluded from the study. Also, participants with central dominant sleep apnea (more than 50% central apnea and hypopneas) were excluded from the study.

Daytime polysomnography was performed for the convenience of participants and the research personnel. Participants were voluntary sleep deprived to less than 4 hours in the night before the study to induce sleepiness in daytime. Scoring sleep stages and arousals were done by specialists using standard techniques and criteria. Thoracoabdominal motion, nasal pressure, and arterial oxyhemoglobin saturation (SaO$_2$) were monitored by respiratory inductance plethysmography, nasal cannulae, and oximetry, respectively. The definition and classification of apneas (cessation of airflow to the lungs for at least 10 s) and hypopneas (>50% decrease in breathing airflow for more than 10 s with blood oxygen desaturation of >3%) were done in accordance with previous standards. To eliminate any potential effect of postural changes on sleep apnea severity, as assessed by Apnea Hypopnea Index (AHI), and other variables, participants slept supine on a single pillow for the entire study period. Sleep studies were scored by personnel blind to fluid measurements, and vice versa.

While participants were in supine position, UA-XSA and NC were measured before sleep and right after waking up from sleep. UA-XSA and the distance from velum to glottis were measured by acoustic pharyngometry. NC was assessed using a measuring tape. A line was drawn just above the cricothyroid cartilage to ensure the measurements before and after sleep were made at the same level.

Neck fluid volume (NFV) measurements in this study relied on the previous observation that the bioelectrical impedance of a tissue is inversely related to its fluid volume, and can be used for non-invasive estimation of fluid volume. In this study, a method based on the bioelectrical impedance of the neck was used to measure the neck fluid volume (NFV) in accordance with the following equation:

$$V = \left(\frac{\rho^2 L^5 C^2}{4\pi R^2}\right)^{1/3} \quad (1)$$

where C is the circumference of the neck, L is the neck length, R is the resistance estimated from the bioimpedance measurement, and $\rho$ is fluid resistivity.

A MP150 Biopac System and EBI100C modules were used to measure the extra-cellular resistance (R). To measure R, two electrodes were placed on the right side of the neck below the right ear and at the base of the neck to measure the voltage drop across the length of the neck. Two other electrodes were placed one inch from the voltage measuring electrodes to inject a low-amplitude (400 µA) current at 50 kHz. At the beginning of the study, with subjects standing and their head in the neutral position, neck length (L in Equation 1) was measured with a measuring tape as the distance between the voltage measuring electrodes.

Both breathing and snoring sounds were recorded using a Sony EMC-44B omni-directional microphone. The microphone was placed over the suprasternal notch using double-sided adhesive tape. The sounds were filtered by a low-pass filter (cut off frequency of 5 kHz) using a Biopac DA100C. After filtering, the sounds were digitized at a sampling rate of 12.5 kHz using a MP150 Biopac System.

This study was part of a randomized, double cross-over protocol to investigate the effects of fluid overloading by saline infusion on sleep apnea severity in men. In a control arm of the protocol, a negligible amount (approximately 100 ml) of saline was infused by an intravenous cannula during sleep to keep the vein open. In comparison, in the intervention arm, approximately 2,000 ml of saline was infused as a bolus just after sleep onset. The saline solution was warmed to body temperature by placing the bag containing the solution in warm water at 37° C.

Participants arrived in the sleep laboratory at noon after a night of sleep deprivation and were instrumented for sleep studies. Randomization of participants into the control or intervention arms was done by a computer-generated randomization table with unequal blocks of 2 and 4. Personnel analyzing the results were kept blind to randomization. Baseline measurements including UA-XSA, NC, and NFV were done in supine position before sleep and just after the participants woke up. Respiratory and snore sounds were recorded continuously during sleep. Participants were crossed over to the other arm of the study one week after the initial session.

Snoring Sound Segmentation and Feature Extraction

Figure 7A:
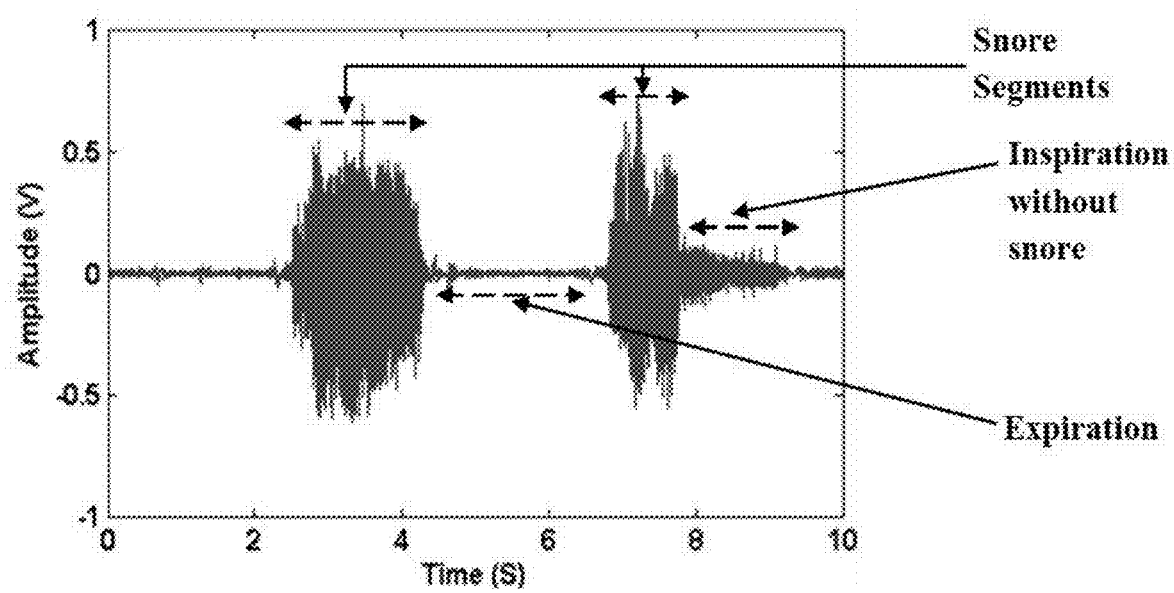
Figure 7B:
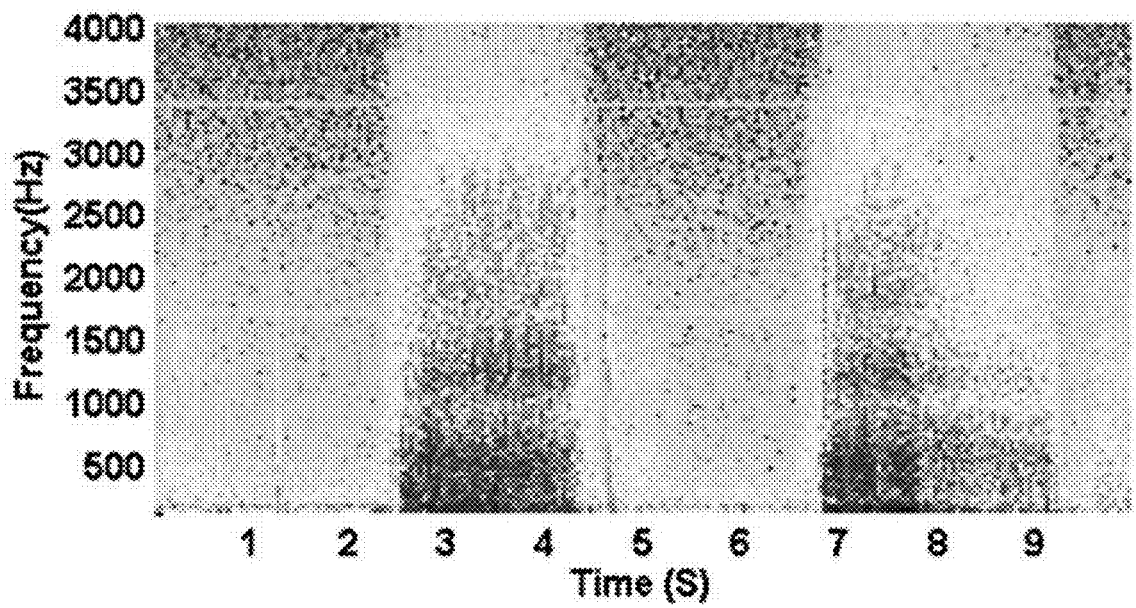
FIG. 7B is a spectrogram of these extracted snoring segments, in accordance with a second example.

Snoring sound segments were extracted manually by an expert by listening to the sounds and observing them in the time-frequency domain, though automated snore segmentation techniques may also be considered in the implementation of an automated breath sound screening device, for example. Likewise, other respiratory sound segmentation processes may be considered to automatically isolate respiratory sound segments of interest, as will be readily appreciated by the skilled artisan, and that, without departing from the general scope and nature of the present disclosure. In this example, a computerized program for labeling audio signals, PRAAT, was used to mark the snore segments. Inspiratory and expiratory snores were marked separately. FIG. 7 shows a 10 second sample of recorded snore and breath sounds, along with the manual annotation of the signal. After manual segmentation of snores, different features in the spectral domain were extracted.

Since sleep stage may change the upper airway control mechanism and the generation of snore sounds, the patterns of snore occurrences were investigated for the entire sleep time and for every sleep stage separately. In this example, only two time-domain features were calculated:

Snoring Percentage (SP), which represents the number of snores in each sleep stage divided by the total number of snores in the entire sleep time; and Snoring Time Index (STI), which represents the total snoring time in each sleep stage divided by the time spent in each sleep stage.

Figure 8A:
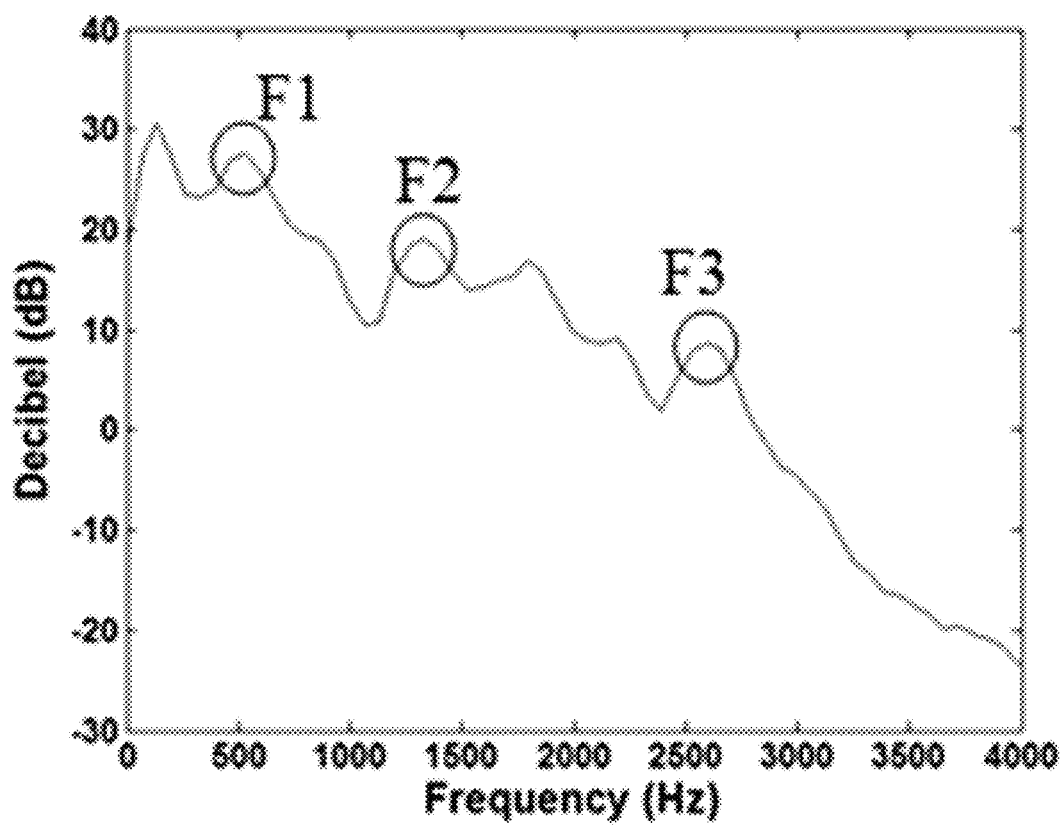

To calculate the spectral features of snores, the snore segments were again band-pass filtered in the frequency range of 100-4000 Hz to remove the effects of heart sound and high frequency noises. In this example, for each snore segment, a pitch frequency (F0), and first, second and third formant frequencies (F1, F2, and F3) were calculated. Considering that snore is a vibratory signal, pitch generally represents the fundamental frequency of the vibration while formant frequencies represent the resonance frequencies. Pitch and formant frequencies were calculated using the validated "Voicebox" toolbox. Pitch frequency was calculated based on the robust algorithm for pitch tracking. For calculation of formants, snore segments were pre-processed using a Hamming window (window size of 20 ms) and a pre-emphasizing filter. Then, $16^{th}$ order linear predictive coding (LPC) spectrum of the snores was estimated. The first three peaks of the LPC spectrum were determined as the formant frequencies (i.e. as shown in FIG. 8a).

Other extracted spectral features included the power of snores in different frequency bands. For instance, the power spectral density (PSD) of each snore segment was calculated based on the Welch method with a Hamming window of 100 ms and 50% overlap between adjacent windows. From the PSD, spectral features were calculated for the entire frequency band (100-4000 Hz), and seven sub-bands: 100-150 Hz, 150-450 Hz, 450-600 Hz, 600-1200 Hz, 1200-1800 Hz, 1800-2500 Hz, and 2500-4000 Hz; the calculated spectral features included the average power of snore sounds in each frequency band; relative power of snore sounds, which is defined as the average power of snores in each sub-band divided by the average power in the entire frequency band (100-4000 Hz); and the spectral centroid of snores, which determines the frequency with the maximum power of snore sounds in each frequency band. Table 4, below, shows the detailed description of each spectral feature. As will be appreciated by the skilled artisan, other spectral features may be considered herein without departing from the general scope and nature of the present disclosure. For example, the above seeks to evaluate different predominant frequency characterizations associated with the isolated snore sound segments, such as the pitch and formant frequencies noted above, as well as the centroid frequencies for each identified frequency ranges. Other frequency characterizations that seek to highlight predominant frequencies in the either frequency band and/or within different constituent frequency ranges may also be considered, as will be appreciated by the skilled artisan.

TABLE 4

Frequency Domain features of the snoring segments

| Feature Name | Method/Equation |
| --- | --- |
| Pitch (F0), Hz | Robust Algorithm for Pitch Tracking (RAPT) |
| Formants (F1, F2, F3), Hz | From LPC analysis |
| Average Signal Power, $P_{avg}$, dB* | $P_{avg}(f_l \leq f \leq f_u) = \sum_{(f_l \leq f \leq f_u)} p(f)\Delta f$ |
| Relative Signal Power (RSP), %* | $\dfrac{P(f_l \leq f \leq f_u)}{P(100 \leq f \leq 4000)}$ |
| Spectral Centroid (SC), Hz* | $\dfrac{\sum_{(f_l \leq f \leq f_u)} fp(f)\Delta f}{P_{avg}(f_l \leq f \leq f_u)}$ |

LPC: Linear predictive Coding
p(f) = Estimated power spectral density
f: Frequency, Hz
$f_l$ = Lower band frequency and $f_u$ = Higher band frequency.
*Feature was computed over the entire frequency band: 100-4000 Hz and seven sub-bands of the power spectrum: 100-150; 150-450; 450-600; 600-1200; 1200-1800; 1800-2500; 2500-4000 Hz.

Modeling of Snore Sound Generation

Figure 8B:
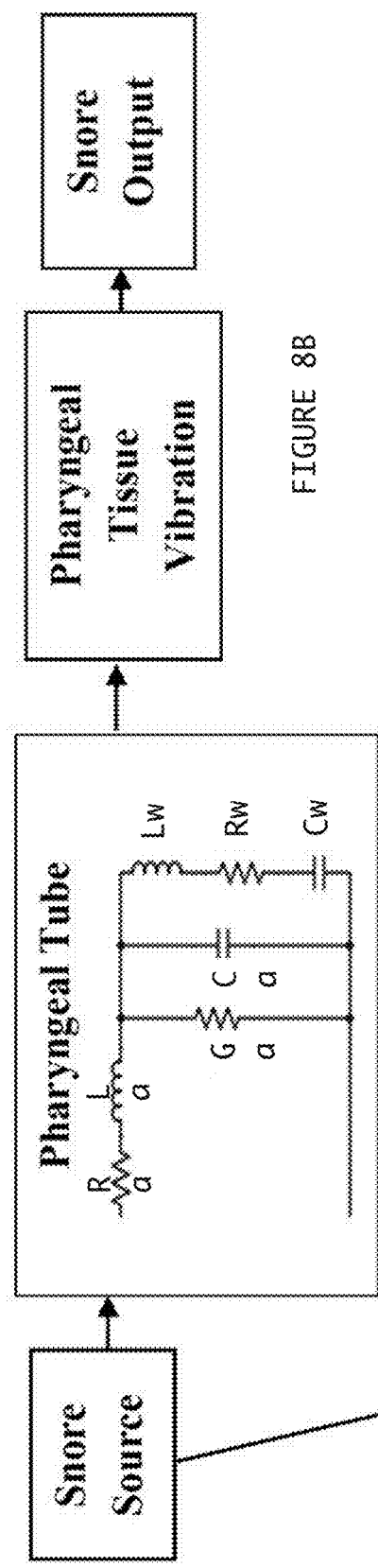
Figure 8C:
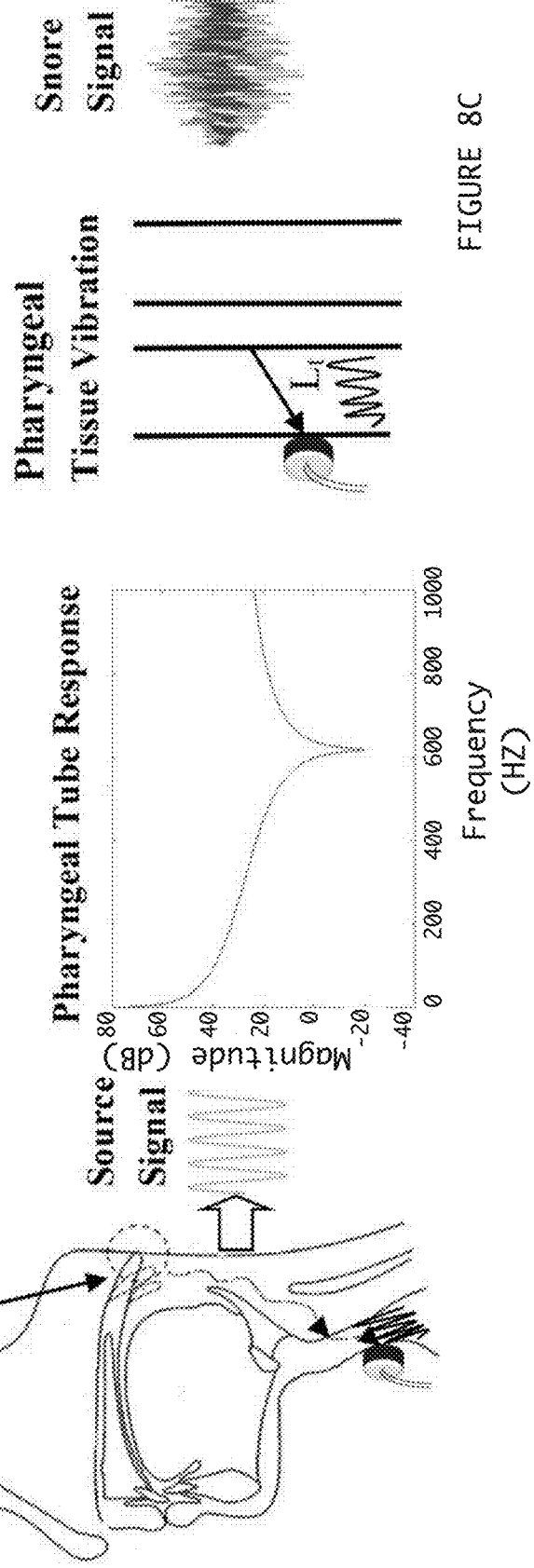
Figure 8D:
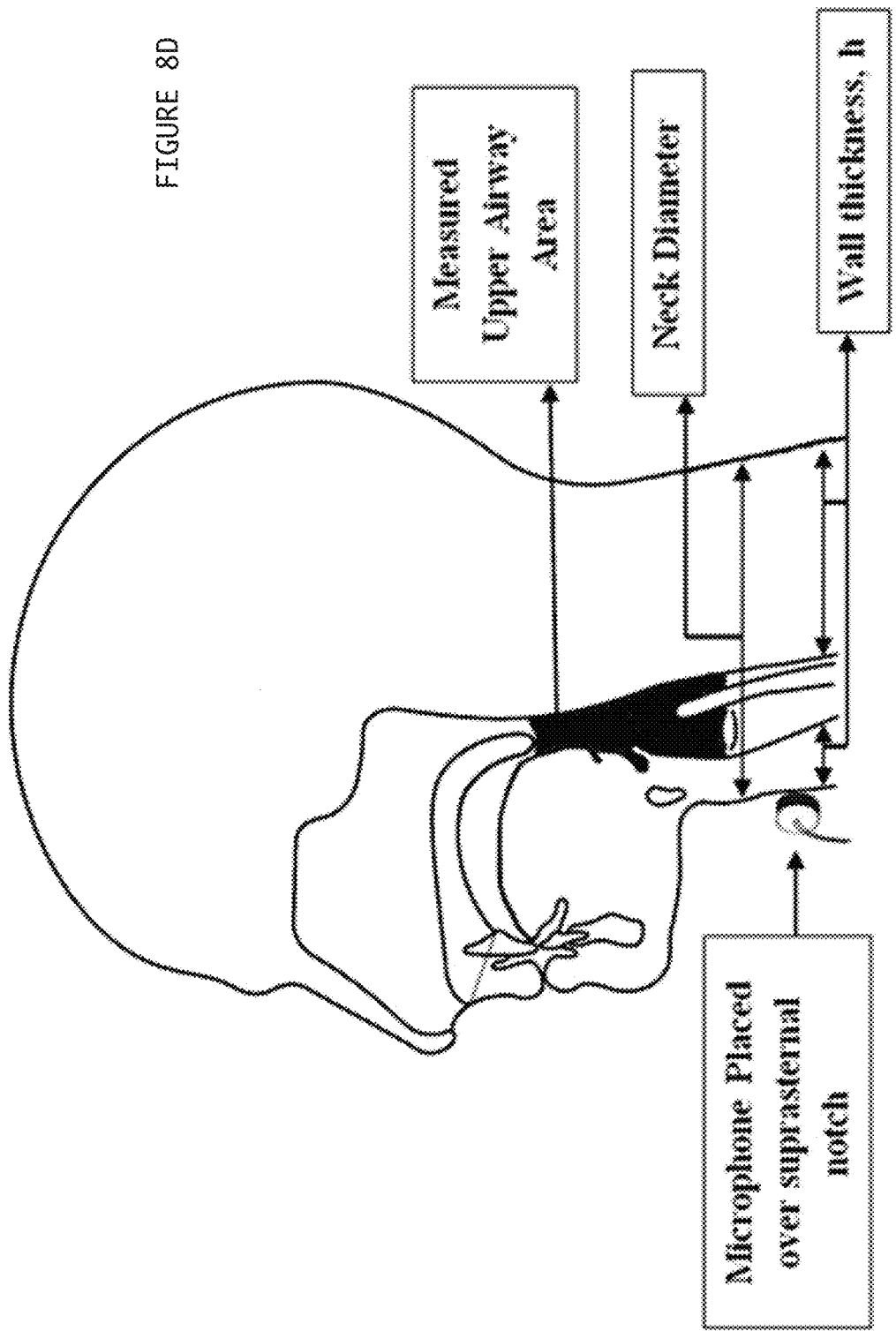

Based on the theory of sound generation in a collapsible tube, as well as the basics of changes in oral cavity for vowel articulations, a simplified three-compartmental model was assumed for snore sound generation, illustrated schematically in FIGS. 8b and 8c. These compartments include snore source, which was assumed to occur due to pharyngeal collapse between the soft palate and epiglottis and the consequent tissue vibration; pharyngeal airway, which was assumed to act as a collapsible tube through which the pressure fluctuation due to snores propagates; and vibrations of the pharyngeal tissue wall that will be transmitted to the microphone located on the suprasternal notch, as schematically illustrated in FIG. 8d. Therefore, snore signals may be modeled as a convolution of snore source, pharyngeal airway and pharyngeal tissue vibration. FIG. 8c schematically illustrates a flow diagram of snore sound generation and propagation, as considered herein and further detailed below.

Snore Source Model

Snoring sound can be generated either by oscillation of the soft palate or pharyngeal wall tissue. Based on the Bernoulli theorem, in a collapsible tube such as pharyngeal airway, increased airflow speed due to narrowed pharynx or increased negative intra-thoracic pressure during inspiration causes a pressure drop along the pharynx, which will further increase the negative pressure in the pharyngeal tube, narrow the pharynx and increase the airflow speed. This sequence of events increases turbulence of airflow within the pharynx, and leads to vibration of the soft palate or the pharyngeal wall tissue; which induces snore sounds. Considering speech articulation, vibration of soft palate or pharyngeal wall during snore sound generation can be assumed to be analogous to the vibration of vocal cord in speech production. Therefore, it can be assumed that the pitch frequency of snore sounds represents the fundamental frequency of snores. Thus, the snore sound source was modeled as a sinusoid signal with frequency equal to the pitch of the snore segment (see FIGS. 8b and 8c).

Pharyngeal Tube Model

From the source, snores propagate through the pharyngeal airway to reach the microphone, which in this example, is placed over the suprasternal notch. In the proposed model, the pharyngeal tube was considered as a single segment, non-rigid, lossy, collapsible tube. FIG. 8b shows the electrical circuit model of the pharyngeal tube, which includes the acoustic losses due to the passage of airflow through the pharynx ($R_a$, $L_a$, $G_a$, $C_a$) as well as the losses due to the collapsible characteristics of pharyngeal wall ($L_w$, $R_w$, $C_w$). In this model, the air pressure and airflow were modeled as the voltage and current, respectively. As mentioned, the input source current to the model was considered as a sinusoid signal with the pitch frequency of the recorded snores for each individual subject. The model includes acoustic resistance of airflow ($R_a$) due to thermal losses, compliance ($C_a$) due to the compression and expansion of air, inertance ($L_a$) due to the mass of air, and resistance due to the heat conduction of the wall ($G_a$); as well as pharyngeal wall resistance ($R_w$), inertance ($L_w$) and compliance ($C_w$) due to the collapsible properties of the pharynx. In this study, previously reported measurements for the air and tissue properties such as viscosity and elasticity were used to calculate model parameters.

Previous models of the pharynx used general values to represent the anatomy of the pharynx such as its radius and wall thickness, which did not incorporate the differences in the pharyngeal anatomy among subjects. In comparison, for each subject in this study, measurements of UA-XSA and NC were used to estimate the pharyngeal radius and pharyngeal wall thickness (FIG. 8d). The pharyngeal tube radius ($T_r$) was calculated as square root of (UA-XSA/π), the neck radius ($N_r$) was estimated based on NC as (2π/NC), and the pharyngeal wall thickness (h) was calculated as ($N_r$-$T_r$).

Validation of the Pharyngeal Tube Model

To validate the proposed model for the pharyngeal tube, the baseline values of UA-XSA, NC, and the distance from velum to glottis were used to simulate variations in the gain and resonance frequency of the electrical circuit model of the pharynx. It was also assumed that variations in the site of the pharyngeal narrowing between velum and glottis would change the effective length of the pharyngeal tube in the proposed model. Based on the proposed model, the effects of changes in UA-XSA, pharyngeal wall thickness (based on changes in NC), and pharyngeal length were calculated on the gain and resonance frequency of the generated snores. To calculate the effect of changes in UA-XSA during sleep, the gain of the circuit for both of the before sleep and after sleep data of UA-XSA were simulated with fixed wall thickness at pre-sleep values for each subject. A similar simulation was performed to see the effect of wall thickness with fixed UA-XSA at pre-sleep values. The simulated results were compared with the formant frequencies and the average power of the recorded snore sounds.

Statistical Analysis

The change in NC, UA-XSA, and NFV from before to after sleep was assessed by paired t-test for normally distributed data and Wilcoxon rank-sum test for non-normally distributed data. The changes in snoring features between different sleep stages were investigated by analysis of variance (ANOVA) and the post-hoc Tukey test. Similarly, variations in average power and relative power of snore sounds between different frequency bands were investigated by ANOVA with the post-hoc Tukey analysis. Correlations between the snoring sound characteristics and changes in baseline measures including UA-XSA, NC and NFV were investigated by Pearson or Spearman's rank coefficient for normally and non-normally distributed data, respectively. To validate the pharyngeal tube model, Pearson correlation coefficients between the simulated resonance frequencies and calculated formant frequencies from every subject were calculated. Furthermore, a Bland-Atlman statistical test was performed to verify agreement between simulated frequencies and recorded formants. Statistical analyses were performed by Matlab and two-tailed $P<0.05$ was considered as significant. Data are presented as mean±STD.

Results

Twenty-one men met all inclusion criteria and were included in this study. Among them, one man did not snore at all and was excluded from the study. Table 5, below, shows the baseline characteristics of the subjects. Although this was a daytime study, participants slept for an average of 150 minutes (i.e. see Table 6), and 14 out of 20 men had at least one full sleep cycle, including both REM and non-REM sleep stages. Subjects spent most of the sleep time in stage N2 (Table 6, $P<0.001$). Subjects were identified to exhibit a wide range of sleep apnea severity, with their AHI ranging from 2 to 86.2 events per hour of sleep. Among the subjects, nine had no or mild sleep apnea (AHI<15), five had moderate sleep apnea (15≤AHI<30) and six had severe sleep apnea (AHI≥30).

TABLE 5

Characteristics of the Participants (n = 20)

| Variable | Mean ± STD |
|---|---|
| Age, years | 45.1 ± 11.4 |
| Height, cm | 176.9 ± 6.3 |
| Weight, kg | 79.0 ± 10.7 |
| Body Mass Index, kg/m$^2$ | 25.4 ± 3.05 |
| Neck circumference, cm | 41.8 ± 2.9 |
| Upper Airway Cross-Sectional Area, cm$^2$ | 2.6 ± 0.6 |
| Neck Fluid Volume, ml | 265.7 ± 49.5 |
| Velum to Glottis length, cm | 9.1 ± 1.8 |
| Systolic Blood Pressure, mmHg | 110.6 ± 8.5 |
| Diastolic Blood Pressure, mmHg | 76.0 ± 8.3 |

From before and after sleep, there were significant increases in NC (i.e. see Table 6; ΔNC: 0.5±0.3 cm, $P<0.001$) and NFV (ΔNFV: 18.6±6.9 ml, $P<0.001$) and a decrease in UA-XSA (ΔUA-XSA: -0.4±0.3 cm$^2$, $P<0.001$). The percentage increases in NFV had significant correlations with the percentage reduction in UA-XSA (r=-0.54, P=0.017). These results complied with previous studies that fluid accumulation in the neck during sleep can narrow the UA-XSA. However, while there was a trend for positive correlation between increases in NFV and NC, it was not statistically significant (r=0.359, P=0.188).

TABLE 6

| | Sleep Structure | |
|---|---|---|
| | Variable | Mean ± STD |
| Sleep Structure | Total sleep time, min | 150.1 ± 46.1 |
| | N1 sleep, % | 18.0 ± 10.4 |
| | N2 sleep, % | 57.2 ± 15.1* |
| | N3 sleep, % | 11.5 ± 12.9 |
| | REM sleep, % | 10.7 ± 8.1 |
| | Sleep efficiency, % | 74.7 ± 15.0 |
| | Total AHI, /h | 27.6 ± 25.8 |
| | Obstructive AHI, /h | 25.5 ± 25.7 |
| | Central AHI, /h | 2.0 ± 2.67 |
| Changes in Baseline Measures | ΔNC, cm | 0.5 ± 0.3* |
| | ΔUA-XSA, cm$^2$ | -0.4 ± 0.3* |
| | ΔNFV, ml | 18.6 ± 6.9* |

*p < 0.01

Temporal Patterns of Snores Overnight

An average of 342±223 snores was manually extracted from the entire sleep time for every individual (134.2±96.0 snores per hour of sleep). While the number of snores in the stage N2 of sleep was significantly higher than other sleep stages ($P<0.001$); this was driven by the fact that subjects spent most of their time in stage N2. Consequently, when the number of snores was normalized by the time spent in each sleep stage, the snore time index was similar for different sleep stages ($P>0.10$). Similarly, the snore time index was similar in both non-REM sleep and REM sleep ($P>0.10$).

There were significant positive correlations between baseline NC measured before sleep and the snore time index in N1 and N2 sleep stages (N1: r=0.52, P=0.019; N2: r=0.55, P=0.012). But, there were no significant correlations between pre sleep NC and snore time index during N3 or REM sleep stages ($P>0.10$ for both). Therefore, subjects with larger baseline NC, spent more time snoring in N1 and N2 sleep stages. However, there were no significant correlations between either snore percentage or snore time index and UA-XSA or NFV.

Spectral Features of Snores

Figure 9A:
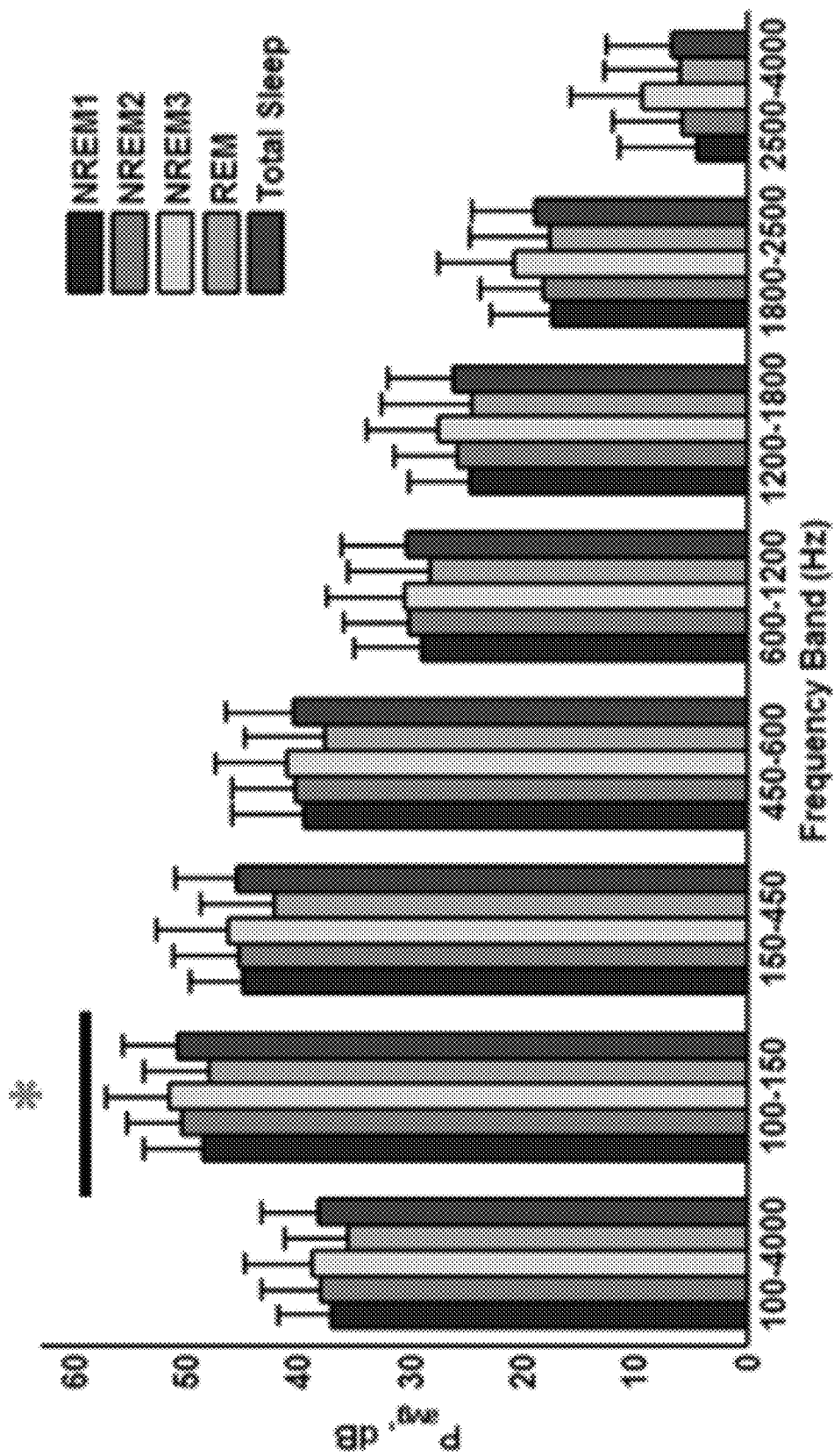
Figure 9B:
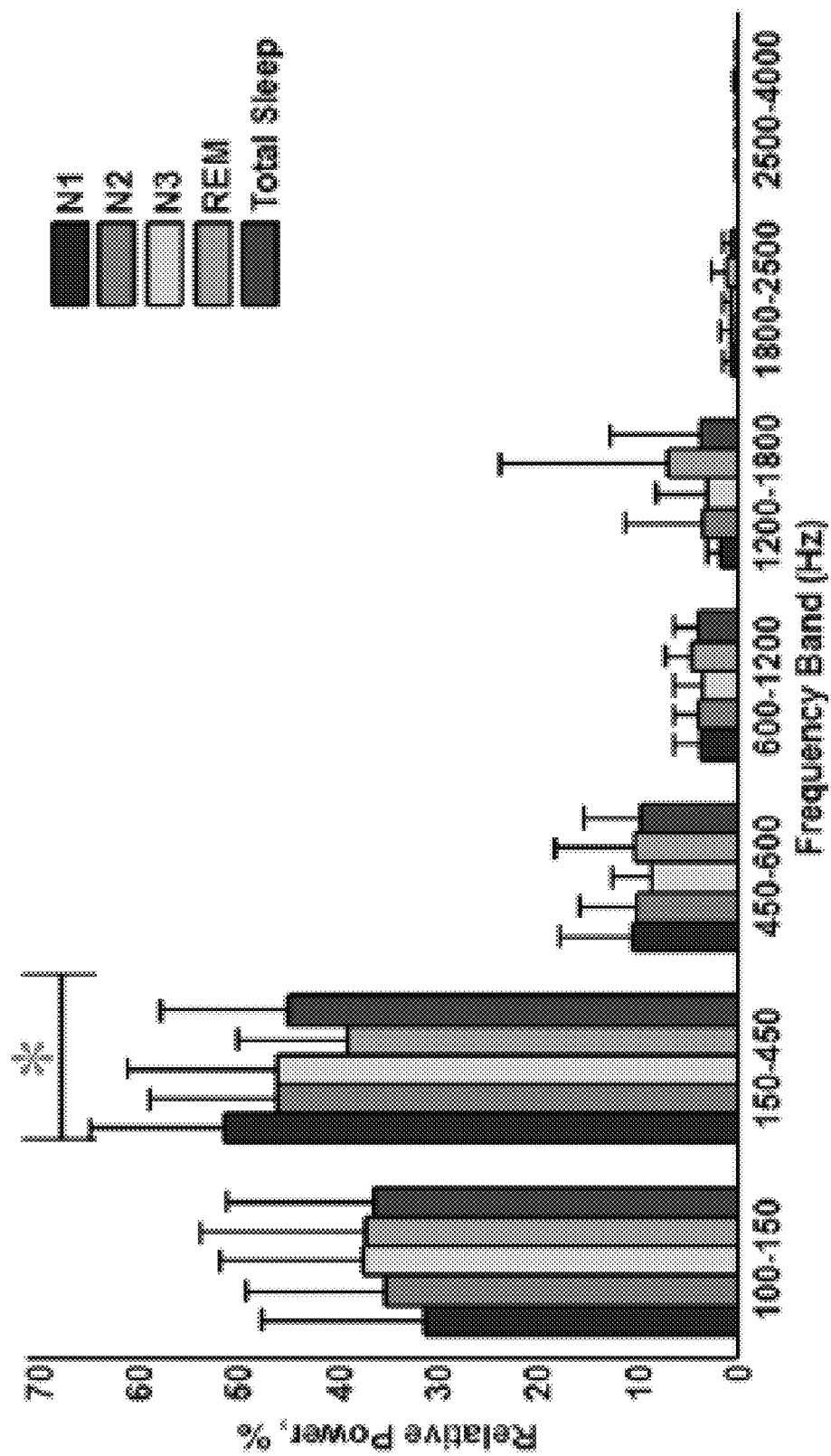
FIG. 9B is a plot of an average and standard deviation of relative snoring power in various frequency ranges for different sleep stages.

The average power of snores was 38.2±5 dB for the total frequency band of 100-4000 Hz. The relative power in the frequency range of 150-450 Hz was significantly higher than other bands in all the sleep stages and total sleep ($P<0.001$). There was a positive correlation between the relative power of snore sounds in the frequency range of 150-450 Hz and AHI (i.e. see FIGS. 9a and 9b; r=0.48, P=0.039). Within each frequency band, the average power, relative power and spectral centroid of snore sounds were similar between different sleep stages.

Figure 13A:
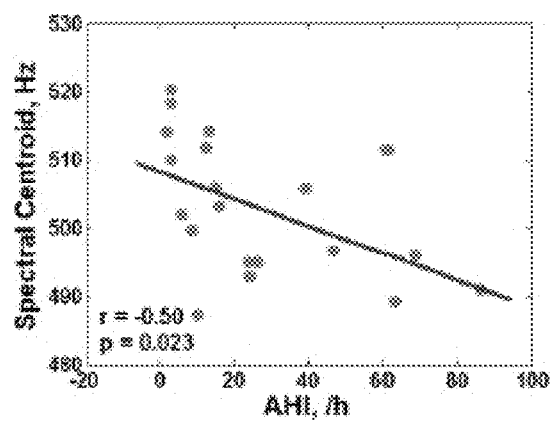
FIG. 13A is a plot illustrating a relationship between an apnea-hypopnea index (AHI) and spectral centroid of snoring sounds (calculated over the entire sleep duration) within 450-600 Hz frequency range.
Figure 13B:
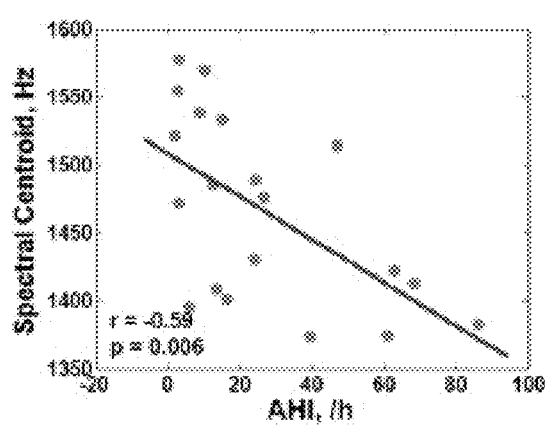
FIG. 13B is a plot illustrating a relationship between AHI and spectral centroid of snoring sounds (calculated over the entire sleep duration) within 1200-1800 Hz frequency range.
Figure 13C:
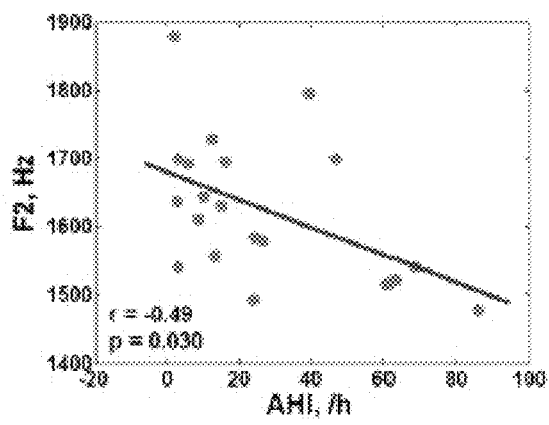
FIG. 13C is a plot illustrating a relationship between AHI and a 2nd formant of the snoring sounds.

The average F1, F2 and F3 were 572.1±122.6 Hz, 1626.1±168.7 Hz and 2608.5±169.3 Hz, respectively. Formant frequencies were similar between different sleep stages as well. There was a significant and negative correlation between F2 and AHI (i.e. see FIG. 13c; r=-0.49, P=0.030). Formant frequencies are associated with spectral centroids in the corresponding frequency ranges. The association between F2 and AHI was supported by a negative correlation between the spectral centroid of snores in the frequency range of 1200-1800 Hz and AHI (i.e. see FIG. 13b, r=-0.59, P=0.006). AHI was also negatively correlated with the spectral centroid in 450-600 Hz (i.e. see FIG. 13a; r=-0.52, P=0.022).

Figure 13D:
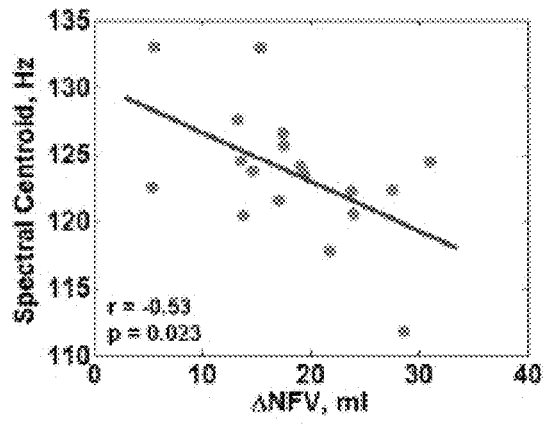
FIG. 13D is a plot illustrating a relationship between percentage change in neck fluid volume (NFV) and spectral centroid of snoring sounds (calculated over the entire sleep duration) within 100-150 Hz frequency range.

The average pitch frequency of the snores was 102.1±20.6 Hz for entire sleep, which could be associated with the spectral centroid of snores in the frequency range of 100-150 Hz. There was a significant and negative correlation between increases in NFV from before to after sleep and the spectral centroid of snores in the frequency range of 100-150 Hz (i.e. see FIG. 13d; r=−0.47, p=0.037) for total sleep. Similar correlations were found between ΔNFV and spectral centroids of snores during N1 (r=−0.51, p=0.03) and N3 (r=−0.52, P=0.05) sleep stages.

Effects of Passive Anatomy of Pharynx on Snores

Figure 10B:
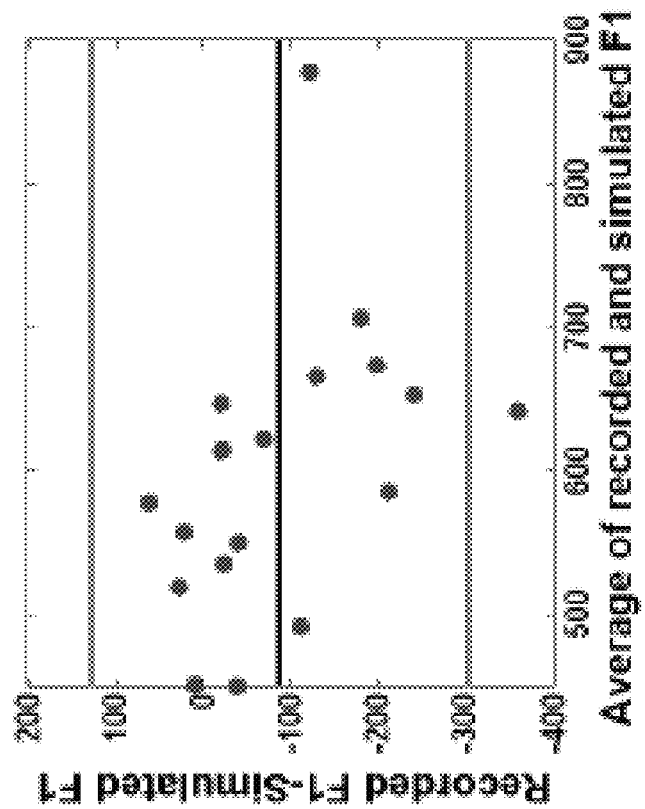
FIG. 10B is a Bland-Altman plot between the F1 of the recorded snores and the simulated formants, wherein the middle (black) line indicates an average difference and the opposed (red) lines present the mean±1.96 of standard deviation (boundaries of 95% confidence interval) of the difference.
Figure 10A:
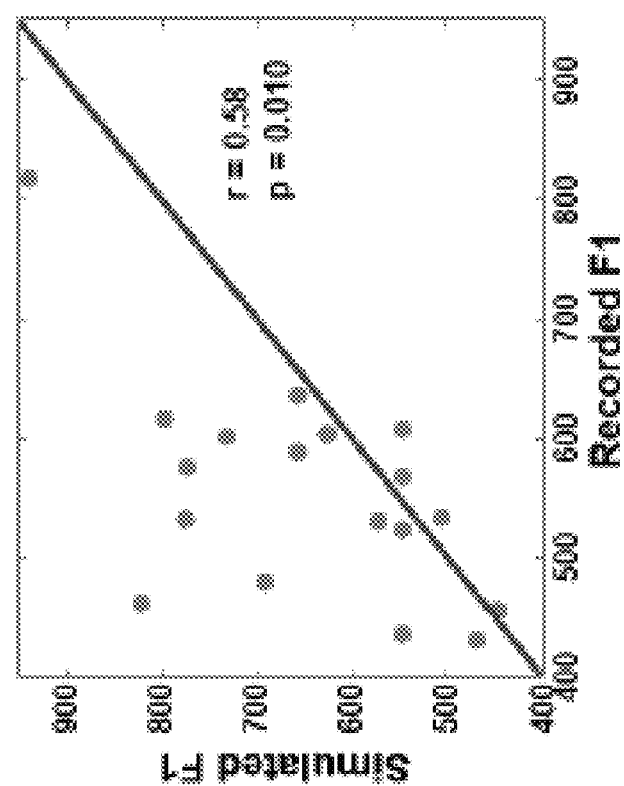

For every individual, the baseline measurements of UA-XSA, NC, and the distance between velum to glottis before sleep (i.e. see Table 7, below) were used to simulate the formant frequencies of snore sounds. FIG. 10a shows the relationship between the simulated F1 and recorded F1 (average F1 of all recorded snores from every individual). There was a strong correlation between the simulated and recorded F1 (r=0.58, P=0.010). FIG. 10b shows the results of the Bland-Atlman test to investigate the agreement between simulated and recorded F1. The average and two standard deviation of difference were −87.8 and 214.5 respectively; only 1 out of 19 subjects was outside of the 95% confidence interval. Similarly, when instead of pre-sleep measurements, post-sleep measurements of UA-XSA, NC and velum to glottis distance were used in the proposed model, the correlation between simulated and recorded F1 was significant (r=0.59, P=0.008). These results indicated the validity of the proposed model for pharyngeal tube to investigate the variation in snore sound resonance frequencies.

TABLE 7

Range of values obtained from the subjects for using in different equations of the electrical circuit model

| Parameter | Symbol | Range |
|---|---|---|
| Cross Sectional Area | A, cm$^2$ | Before Sleep: 1.23 to 3.87 |
| | | After Sleep: 1.02 to 3.24 |
| Tube Radius | $T_r$, cm | Before Sleep: 0.62 to 1.10 |
| | | After Sleep: 0.56 to 1.01 |
| Tube length | l, cm | Before Sleep: 7 to 12.6 |
| | | After Sleep: 6.43 to 12.1 |
| Wall Thickness | h, cm | Before Sleep: 4.9 to 6.6 |
| | | After Sleep: 5.1 to 6.8 |

Figure 11:
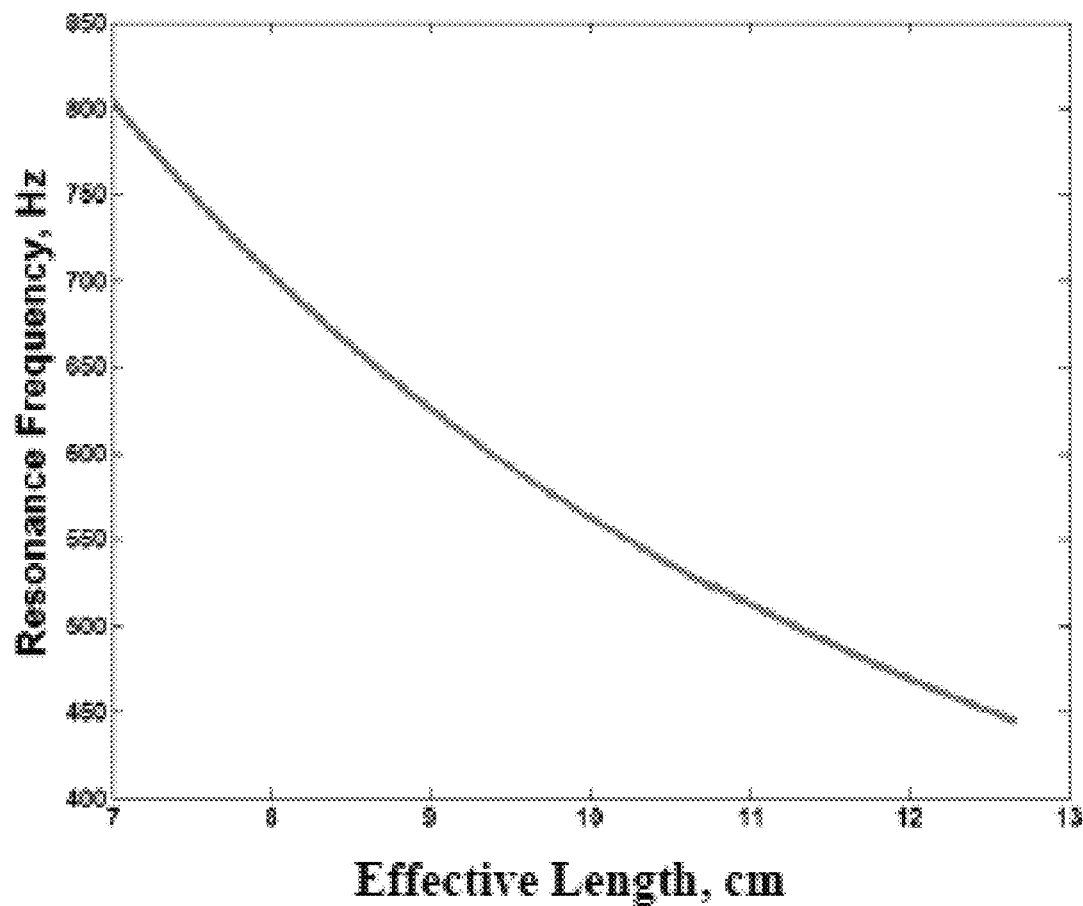
FIG. 11 is a plot illustrating a relationship between effective length and resonance frequencies.

FIG. 11 shows the modeling results for the relationship between the pharyngeal airway effective length, modeled as the distance between the glottis and the potential collapse site in pharyngeal airway, and F1 frequency. Increasing the effective length from 7 cm to 12.5 cm (which was the range of velo-glottal length in our subjects), the F1 frequency decreased from 800 Hz to 450 Hz.

Effects of Changes in Upper Airway Anatomy During Sleep on Snoring Power

Figure 12A:
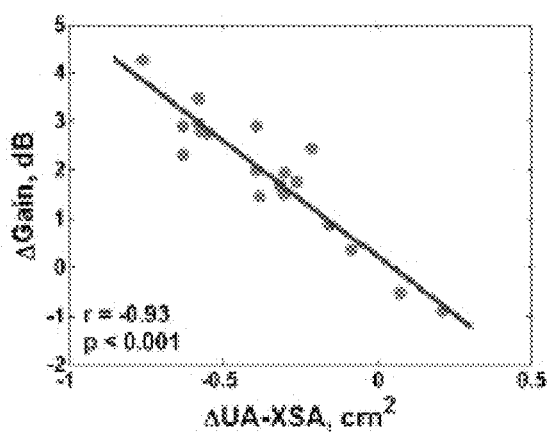
FIG. 12A is a plot illustrating a relationship between change in cross sectional area and change in gain of pharyngeal tube model.
Figure 12B:
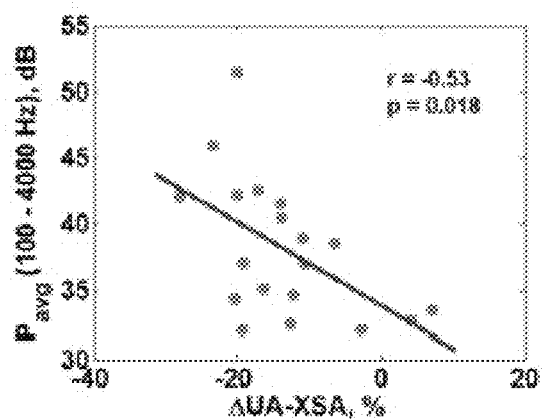
FIG. 12B is a plot illustrating a relationship between percentage change in upper airway cross-section area (UA-XSA) and average power of snoring sounds (calculated over the entire sleep duration) within 100-4000 Hz frequency range.
Figure 12C:
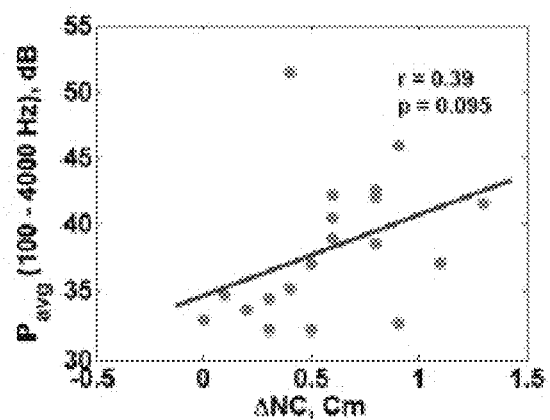
FIG. 12C is a plot illustrating a relationship between percentage change in NC and average power of snoring sounds (calculated over the entire sleep duration) within 100-4000 Hz frequency range.

The gain of pharyngeal tube was simulated based on variations in UA-XSA and pharyngeal wall thickness (due to changes in NC from before to after sleep) during sleep. Narrowing in the UA-XSA from before to after sleep was significantly correlated with an increase in the gain of pharyngeal tube model (i.e. see FIG. 12a; r=−0.93, P<0.001). On the other hand, there was no significant correlation between changes in wall thickness and gain of the pharyngeal tube model (P>0.10). These modeling results complied with those achieved from the recorded snore sounds. Based on the recorded snores, narrowing in the UA-XSA during sleep was found to be significantly correlated with increases in the average power of snore sounds in the frequency range of 100-4000 Hz (i.e. see FIG. 12b; r=−0.53, P=0.018) as well as 100-150 Hz (r=−0.52, P=0.020) and 150-450 Hz (r=−0.47, P=0.049). On the other hand, there were no significant correlation between average power of snore sounds in various frequency ranges and increases in the NC after sleep which could be associated with the changes in pharyngeal wall thickness (i.e see FIG. 12c, P=0.1).

The above study provides a realistic acoustic model of the upper airway in describing the generation and propagation of snore sounds. In particular, the pharynx was modeled as a collapsible tube, and the effects of changes in its anatomy such as cross sectional area, wall thickness, and length were investigated on spectral and temporal features of generated snores. The proposed model was further validated based on the recorded snores during sleep. As reported above, the proposed model predicts that upper airway narrowing during sleep can increase snore sound average power, while changes in the length of the upper airway can decrease the resonance frequency of snore sounds. These modeling results were further validated based on the recorded snore sounds. Furthermore, it was found that resonant frequencies of the snores, which depend on the length and potential site of collapse in the upper airway, were strongly correlated to sleep apnea severity.

The proposed acoustic model for the snore sound generation and propagation includes snore source, propagation of snores through the upper airway, and its transmission to the microphone over the neck, in the illustrated example. Snore source was modeled as a single frequency vibratory signal due to either soft palate vibration or pharyngeal tissue vibration at the site of upper airway narrowing. Similar to speech articulation, pitch frequency of snores was considered as the main vibrating frequency of the snore source. The pitch frequency of recorded snores was found to be lower than 150 Hz. Furthermore, the proposed model is subject-specific and for every individual, the pitch frequency of recorded snores was used to simulate the source of snore generation.

In the proposed model, the upper airway was considered to be a collapsible tube. Based on this model, snore sound features would change due to both the acoustic changes in the airflow velocity as it passes through the pharynx and the effects of the pharyngeal wall vibrations on the airflow. An important finding of the proposed model, which was also supported based on the recorded snores, was that narrowing in the upper airway increases the average power of snores. Narrowing in the upper airway increases sleep apnea severity. The results presented herein also showed that in patients with higher AHI, the relative power of snore sounds in low frequency components was higher. These results highlight the possible application of using snore sound average power to predict severity of upper airway narrowing in patients with obstructive sleep apnea.

Another finding was that the length of the pharyngeal tube was inversely correlated to the response frequency (F1) of the snore sounds. In vowel articulation, F1 is associated with the posterior movement of the tongue toward the base of the oral cavity, which could narrow the pharyngeal airway.

As snore sound and speech sound propagate through the same pharyngeal airway, formant frequencies can carry a vital role in characterizing the snore sounds. Therefore, formant frequencies of the snores may be used to represent variations in the pharyngeal airway due to the position of the tongue. Posterior movements of the tongue could reflect narrowing in the pharyngeal airway. Based on the sound generation in a collapsible tube, if the narrowing occurs in a side where the sound propagates from the source it increases the effective length of the tube. Therefore, pharyngeal airway narrowing may increase the effective pharyngeal length.

In a solid tube, the resonance frequency of sound is related to the speed of sound and inversely related to the length of the tube, F2 is associated with the advancement of the tongue and F3 is associated with the degree of lip rounding.

Furthermore, it was found that AHI was negatively correlated with the formant frequencies of snores. Recent imaging studies have shown that, sleep apnea patients have a larger pharyngeal length and thicker tongue with more collapsible airway than normal subjects even during wakefulness. This means patients with high AHI have a longer pharyngeal length than patients with low AHI. Considering this fact, it can be speculated from the above-described model that patients with high AHI may have lower formant frequencies. This speculation complies with the findings obtained from the recorded snores. It was found that a larger AHI was associated with a lower F2. Also, AHI was negatively correlated with the spectral centroid in the 450-600 Hz (which may correspond to F1 of the snores) and 1200-1800 Hz (which may correspond to F2 of the snores) frequency ranges. Furthermore, previous studies have reported that an increase in fluid accumulation in the neck is significantly correlated with an increase in the AHI. Therefore, increases in NFV during sleep may be another underlying reason for decreasing in the formant frequencies.

To understand the direct effect of NFV, the increasing in NFV from before to after sleep was also assessed on the spectral frequencies. It was found that increases in NFV during sleep were significantly correlated with decreases in the spectral centroid in 100-150 Hz (which may correspond to the pitch or fundamental frequency of the snores).
Therefore, fluid accumulation in the neck could decrease the fundamental frequency of the snores. This may be due to the fact that fluid accumulation in the neck during sleep may increase pharyngeal tissue pressure around the pharyngeal airway and may have an effect on the pharyngeal wall vibration on generation of snore sounds.

Ultimately, this illustrative study presented underlying anatomical effects of the upper airway on snoring sound features, which features can be used to effectively and accurately contribute to automated sleep apnea screening and diagnostic tools.

While the present disclosure describes various exemplary embodiments, the disclosure is not so limited. To the contrary, the disclosure is intended to cover various modifications and equivalent arrangements included within the general scope of the present disclosure.

What is claimed is:

1. A non-invasive method for assessing upper airway anatomy in a subject while breathing to output an indication on sleep apnea severity, the method comprising:
   receiving as input at a hardware processor a digital signal representative of respiratory sounds generated by the subject while breathing;
   isolating digital respiratory sound segments of interest from said digital signal;
   computationally extracting a designated spectral feature from each of said segments to characterize said respiratory sound within each of said segments;
   automatically evaluating each said extracted spectral feature against a preset upper airway anatomy dimension metric defined by a pre-established scale automatically correlating said extracted spectral feature with a given upper airway anatomy measure to characterize said given upper airway anatomy measure in the subject while breathing; and
   outputting a sleep apnea severity indication based on said characterized upper airway anatomy measure.

2. The method of claim 1, wherein said digital respiratory sound segments are snoring sound segments.

3. The method of claim 2, wherein said designated spectral feature is an average snoring sound power within a given frequency range, and wherein said upper airway anatomy metric is a neck circumference variation metric defined by a pre-established snoring power scale automatically correlating a relatively higher snoring power with a correspondingly larger neck circumference increase.

4. The method of claim 3, wherein said frequency range is selected from one of 100-4000 Hz, 100-150 Hz, 150-450 Hz and 450-600 Hz.

5. The method of claim 3, wherein said frequency range is 150-450 Hz.

6. The method of claim 2, wherein said designated spectral feature is a predominant snoring frequency, and wherein said upper airway anatomy dimension metric is an effective pharyngeal length metric defined by a pre-established frequency scale automatically correlating a relatively lower predominant frequency with a correspondingly greater effective pharyngeal length.

7. The method of claim 6, wherein said predominant frequency comprises at least one of a pitch frequency, a first formant frequency and a second formant frequency of said snoring sound segments.

8. The method of claim 7, wherein said predominant frequency comprises a spectral centroid within at least one of the following frequency ranges: 1200-1800 Hz, 450-600 Hz, and 100-150 Hz.

9. The method of claim 2, wherein said designated spectral feature is a predominant snoring frequency, and wherein said upper airway anatomy metric is a neck fluid volume NFV variation defined by a pre-established NFV scale automatically correlating a relatively lower predominant frequency with a correspondingly greater NFV increase.

10. The method of claim 9, wherein said predominant frequency comprises a pitch frequency of said snoring sound segments.

11. A non-invasive method for evaluating sleep apnea severity, the method comprising:
    receiving as input at a hardware processor a digital signal representative of respiratory sounds generated by the subject while breathing;
    isolating digital snoring sound segments from said digital signal;
    computationally extracting a designated spectral feature from each of said segments to characterize said snoring sounds within each of said segments;
    automatically evaluating each said extracted designated spectral feature against a preset sleep apnea severity metric associated with said designated spectral feature; and
    outputting a sleep apnea severity indication based on said automatically evaluating;
    wherein said designated spectral feature comprises a predominant snoring frequency, and wherein said automatically evaluating comprises correlating a relatively lower predominant snoring frequency-with a correspondingly higher sleep apnea severity.

12. A non-invasive upper airway anatomy assessment device to output an indication on sleep apnea severity comprising:
    an acoustic signal input interface;
    a digital storage device having stored thereon a hardware processor operable upper airway assessment engine operable to access an upper airway anatomy dimension metric defined by a pre-established scale automatically correlating a designated respiratory sound spectral feature with a given upper airway anatomy measure; and a hardware processor operable to execute said hardware processor operable upper airway assessment engine to:

receive as input a digital signal representative of respiratory sounds generated by a given subject while breathing;

isolate digital respiratory sound segments from said digital signal;

extract said designated spectral feature from each of said segments to characterize said respiratory sounds within each of said segments;

evaluate each said extracted spectral feature against said upper airway anatomy dimension metric to characterize said given upper airway anatomy measure of the given subject while breathing; and output a sleep apnea severity indication based on said given upper airway anatomy so characterized.

13. The device of claim 12, wherein said designated respiratory sound spectral feature is a designated snoring sound spectral feature, and wherein said digital respiratory sound segments are snoring sound segments.

14. The device of claim 13, further comprising a microphone operatively coupled to said acoustic signal input interface and to be located in an area of the given subject while breathing to capture said respiratory sounds and generate said digital signal representative thereof.

15. The device of claim 13, wherein said designated spectral feature is an average snoring sound power within a given frequency range, and wherein said metric is a neck circumference variation metric defined by a pre-established snoring power scale automatically correlating a relatively higher snoring power with a correspondingly larger neck circumference increase.

16. The device of claim 13, wherein said designated spectral feature is a predominant snoring frequency, and wherein said upper airway dimension metric is an effective pharyngeal neck length metric defined by a pre-established frequency scale automatically correlating a relatively lower predominant frequency with correspondingly longer effective pharyngeal neck length.

17. The device of claim 16, wherein said predominant frequency comprises at least one of a pitch frequency, a first formant frequency and a second formant frequency of said snoring sound segments.

18. The device of claim 13, wherein said designated spectral feature is a predominant frequency, and wherein said metric is a neck fluid volume NFV variation metric defined by a pre-established NFV scale automatically correlating a relatively lower predominant frequency with a correspondingly greater NFV increase.

19. The device of claim 18, wherein said predominant frequency comprises a pitch frequency of said snoring sound segments.

20. A non-transitory computer-readable medium having statements and instructions stored therein for execution by a processor to execute an upper airway assessment to output an indication on sleep apnea severity by:

receiving as input a digital signal representative of respiratory sounds generated by a given subject while breathing;

isolating digital respiratory sound segments from said digital signal;

extracting a designated spectral feature from each of said segments to characterize said respiratory sounds within each of said segments;

accessing an upper airway anatomy dimension metric defined by a pre-established scale automatically correlating said designated spectral feature with a given upper airway anatomy measure;

evaluating each said extracted spectral feature against said upper airway anatomy dimension metric to characterize said given upper airway anatomy measure of the given subject while breathing; and outputting a sleep apnea severity indication based on said given upper airway anatomy measure so characterized.

21. The non-transitory computer-readable medium of claim 20, wherein said digital respiratory sound segments are snoring sound segments.

22. The non-transitory computer-readable medium of claim 21, wherein said designated spectral feature is a predominant snoring frequency, and wherein said upper airway dimension metric is an effective pharyngeal neck length metric defined by a pre-established frequency scale automatically correlating a relatively lower predominant frequency with a correspondingly longer effective pharyngeal neck length.

23. The method of claim 11, wherein said upper airway dimension metric comprises an effective pharyngeal neck length metric defined by a pre-established frequency scale automatically correlating said relatively lower predominant frequency with a correspondingly longer effective pharyngeal neck length.

* * * * *